United States Patent
Srivastava et al.

(10) Patent No.: US 11,913,076 B2
(45) Date of Patent: Feb. 27, 2024

(54) PROSTATE CANCER GENE PROFILES AND METHODS OF USING THE SAME

(71) Applicant: THE HENRY M. JACKSON FOUNDATION FOR THE ADVANCEMENT OF MILITARY MEDICINE, INC., Bethesda, MD (US)

(72) Inventors: Shiv K. Srivastava, Potomac, MD (US); Gyorgy Petrovics, Bethesda, MD (US); Indu Kohaar, North Potomac, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 172 days.

(21) Appl. No.: 16/611,692

(22) PCT Filed: May 8, 2018

(86) PCT No.: PCT/US2018/031550
§ 371 (c)(1),
(2) Date: Nov. 7, 2019

(87) PCT Pub. No.: WO2018/208749
PCT Pub. Date: Nov. 15, 2018

(65) Prior Publication Data
US 2021/0108271 A1 Apr. 15, 2021

Related U.S. Application Data

(60) Provisional application No. 62/505,798, filed on May 12, 2017.

(51) Int. Cl.
*C12Q 1/68* (2018.01)
*C07H 21/04* (2006.01)
(Continued)

(52) U.S. Cl.
CPC .......... *C12Q 1/6886* (2013.01); *G16B 25/10* (2019.02); *G16B 25/20* (2019.02); *C12Q 2600/158* (2013.01)

(58) Field of Classification Search
None
See application file for complete search history.

(56) References Cited

U.S. PATENT DOCUMENTS

2013/0344487 A1* 12/2013 Fradet .................. C12Q 1/6886
435/6.11
2015/0024949 A1* 1/2015 Russo .................. C12Q 1/6886
435/6.12
(Continued)

FOREIGN PATENT DOCUMENTS

WO 2014/025810 A1 2/2014
WO WO-2018065525 A1 * 4/2018 ........... C12Q 1/6886

OTHER PUBLICATIONS

Brassell et al. The center for prostate disease research (CPDR): A multidisciplinary approach to translational research. Urologic Oncology: Seminars and Original Investigations; 2009; 27: 562-569. (Year: 2009).*

(Continued)

*Primary Examiner* — Jeanine A Goldberg
(74) *Attorney, Agent, or Firm* — MH2 TECHNOLOGY LAW GROUP, LLP

(57) ABSTRACT

The present disclosure provides gene expression profiles that are associated with prostate cancer, including certain gene expression profiles that differentiate between subjects of African and Caucasian descent and other gene expression profiles that are common to subjects of both African and Caucasian descent. The gene expression profiles can be measured at the nucleic acid or protein level and used to stratify prostate cancer based on ethnicity. The gene expression profiles can also be used to identify a subject for (Continued)

prostate cancer treatment. Also provided are kits for diagnosing and prognosing prostate cancer and an array comprising probes for detecting the unique gene expression profiles associated with prostate cancer in subjects of African and/or Caucasian descent.

5 Claims, 17 Drawing Sheets

(51) Int. Cl.
C12Q 1/6886 (2018.01)
G16B 25/20 (2019.01)
G16B 25/10 (2019.01)

(56) References Cited

U.S. PATENT DOCUMENTS

2015/0024961 A1* 1/2015 Klass ............... G01N 33/57434
435/7.1
2015/0218646 A1* 8/2015 Haince .................... G16B 40/00
506/17
2016/0326594 A1* 11/2016 Srivastava ....... G01N 33/57434

OTHER PUBLICATIONS

Wang et al. Identification and Functional Validation of Reciprocal microRNA-mRNA Pairings in African American Prostate Cancer Disparities. Clin Cancer Res; 2015; 21(21); 4970-4984. (Year: 2015).*
Nilsson et al. Prostate cancer-derived urine exosomes: a novel approach to biomarkers for prostate cancer. British Journal of Cancer; 2009; 100: 1603-1607. (Year: 2009).*
Hessels and Schalken. Urinary biomarkers for prostate cancer: a review. Asian Journal of Andrology; 2013;15: 333-339. (Year: 2013).*
McKiernan et al. Novel Urine Exosome Gene Expression Assay to Predict High-grade Prostate Cancer at Initial Biopsy. JAMA Oncol.; 2016; 2(7): 882-889. (Year: 2016).*
He et al. Analytical platform evaluation for quantification of ERG in prostate cancer using protein and mRNA detection methods. Journal of Translational Medicine; 2015; 13; 54; 1-14. (Year: 2015).*
Petrovics et al. Potential of ERG expression in post-DRE urine for prostate cancer detection. American Association for Cancer Research, 99th AACR Annual Meeting; 2018; Apr 12-16; San Diego, CA: LB-223: p. 1-2. (Year: 2008).*
Reams et al. Microarray comparison of prostate tumor gene expression in African-American and Caucasian American males: a pilot project study. Infectious Agents and Cancer; 2009; 4(Suppl 1):S3: p. 1-7. (Year: 2009).*
Jia et al. Diagnosis of Prostate Cancer Using Differentially Expressed Genes in Stroma. Cancer Res; 2011; 71(7):2476-2487. (Year: 2011).*
Petrovics et al. Elevated expression of PCGEM1, a prostate-specific gene with cell growth-promoting function, is associated with high-risk prostate cancer patients. Oncogene; 2004: 23: 605-611. (Year: 2004).*
Petrovics et al. Oncogene; 2004: 23: 605-611. (Year: 2004).*
Brassell et al. Urologic Oncology: Seminars and Original Investigations; 2009; 27: 562-569. (Year: 2009).*
Wang et al. Clin Cancer Res; 2015; 21(21); 4970-4984. (Year: 2015).*
Nilsson et al. British Journal of Cancer; 2009; 100: 1603- 1607. (Year: 2009).*
Hessels and Schalken. Asian Journal of Andrology; 2013;15: 333-339 (Review). (Year: 2013).*
He et al. Journal of Translational Medicine; 2015; 13; 54; 1-14. (Year: 2015).*
McKiernan et al. JAMA Oncol.; 2016; 2(7): 882-889. (Year: 2016).*
Reams et al. Infectious Agents and Cancer; 2009; 4; Suppl 1:S3: p. 1-7. (Year: 2009).*
Petrovics et al. American Association for Cancer Research, 99th AACR Annual Meeting; Apr. 12-16, 2008; San Diego, CA: LB-223: p. 1-2. (Year: 2008).*
Donovan et al. Prostate Cancer and Prostatic Diseases; 2015; 18, 370-375. (Year: 2015).*
Quek et al. The Prostate;2015; 75:1886-1895. (Year: 2015).*
Rigau et al. The Prostate; 2010; 70:1760-1767. (Year: 2010).*
Depalma et al. (J. of Cancer, vol. 7, No. 14, pp. 1960-1967, 2016) (Year: 2016).*
Spanu et al. (PLOS One, vol. 9, Issue 10 e109631, Oct. 2014) (Year: 2014).*
Quek et al. (The Prostate, vol. 75, pp. 1886-1895, 2015) (Year: 2015).*
Rigau et al. (The Prostate, vol. 70, pp. 1760-1767, 2010) (Year: 2010).*
Extended Search Report dated Jan. 13, 2021 from corresponding European Patent Application No. 18798896.9, 9 pages.
Kohaar et al., "Abstract 4649: Development of an ethnicity informed gene expression panel with potential to improve prostate cancer diagnosis", Proceedings: AACR Annual Meeting, Apr. 5, 2017, Cancer Research, Jul. 2017, vol. 77, Issue 13 Supplement, 5 pages.
Deng et al., "Long Non-Coding RNA as Potential Biomarker for Prostate Cancer: Is It Making a Difference?", International Journal of Environmental Research and Public Health, Mar. 7, 2017, vol. 14, No. 3, 16 pages.
Reams et al., "Microarray comparison of prostate tumor gene expression in African-American and Caucasian American males: a pilot project", Infectious Agents and Cancer, 2009, vol. 4, No. Suppl. 1, 7 pages.
International Search Report and Written Opinion dated Sep. 13, 2018 from International Application No. PCT/US2018/031550 (Authorized Officer, Shane Thomas), 18 Pages.
Adam et al., "The role of the PCA3 assay in predicting prostate biopsy outcome in a South African setting", BJU International, Apr. 20, 2011, vol. 108, No. 11, pp. 1728-1733.
Ifere et al., "Prostate Cancer Gene Expression Marker 1 (PCGEM1): A Patented Prostate—Specific Non-Coding Gene and Regulator of Prostate Cancer Progression", Recent Patents on DNA & Gene Sequences, 2009, vol. 3, No. 3, pp. 151-163.
Xu et al., "Quantitative expression profile of PSGR in prostate cancer", Prostate Cancer and Prostatic Diseases, 2006, vol. 9, No. 1, pp. 56-61.
Kohaar et al., "A Urine Exosome Gene Expression Panel Distinguishes between Indolent and Aggressive Prostate Cancers at Biopsy", The Journal of Urology, 2021, vol. 205, pp. 420-425.
Shrivastava et al., "Urinary prostate-specific antigen and microseminoprotein-beta levels in men with and without prostate cancer: A prospective cohort study", Indian Journal of Urology, 2020, vol. 36, Issue 1, pp. 50-55.
FDA Approval Letter from Maria Chan to Alan Maderazo for PROGENSA® PCA3 mRNA assay P100033A dated Feb. 13, 2012, 4 pages.
Communication pursuant to Article 94(3) EPC dated Jun. 7, 2023 for corresponding European Application No. 18798896.9, 6 pages.
Kohaar, I. et al., "MP33-12 Development of a Prostate Cancer Gene Expression Panel To Address Racial Differences of Molecular Alterations in Prostate Cancer", Journal of Urology, 2017, vol. 197, No. 4S, Supplement, pp. e421-e422.
Anonymous: "AACR 2017 Proceedings: Abstracts 3063-5947— Google Books", Jun. 2, 2023, XP093051321, Retrieved from the Internet: URL:https://www.google.nl/books/editionAACR_2017_Proceedings_Abstracts_3063_594/7UVUDgAAQBAJ?hl=nl &gbpv=0 [retrieved on Jun. 2, 2023].
Anonymous: "AACR 2017 Proceedings: Abstracts 3063-5947 on Apple Books", Jun. 2, 2023, XP093051326, Retrieved from the Internet: URL:https://books.apple.com/us/book/aacr-2017-proceedings-abstracts-3063-5947/id 1222426058 [retrieved on Jun. 2, 2023].

* cited by examiner

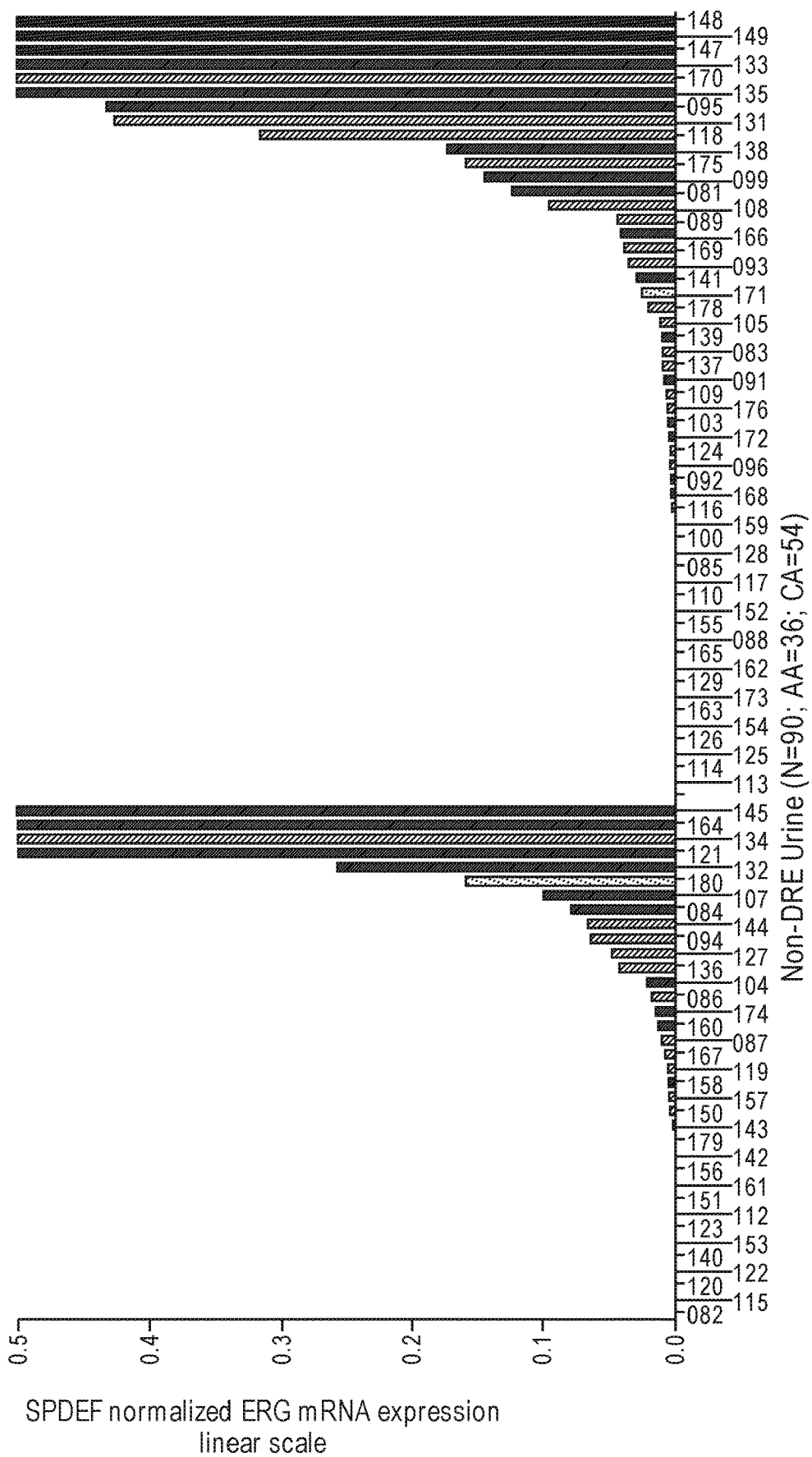

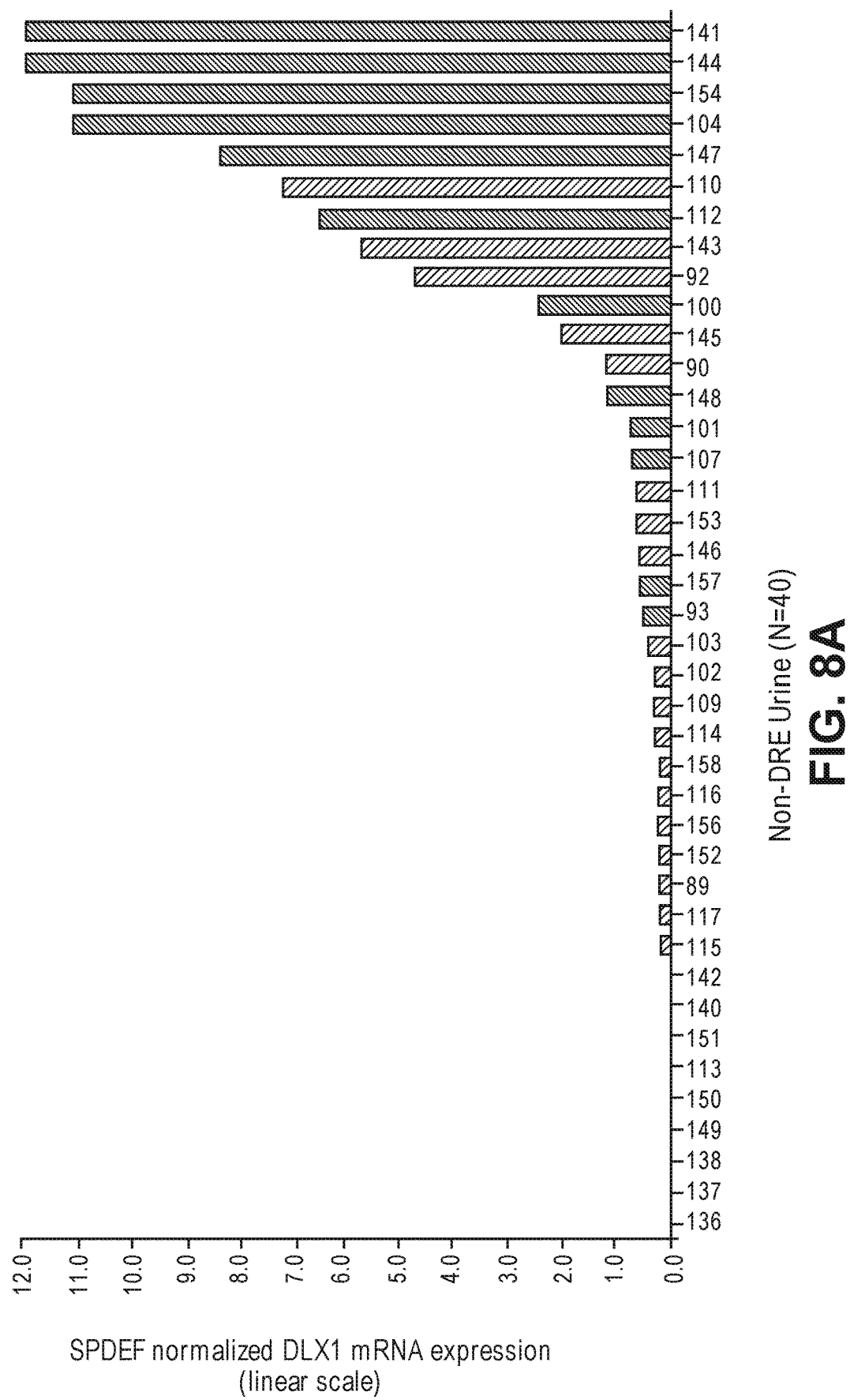

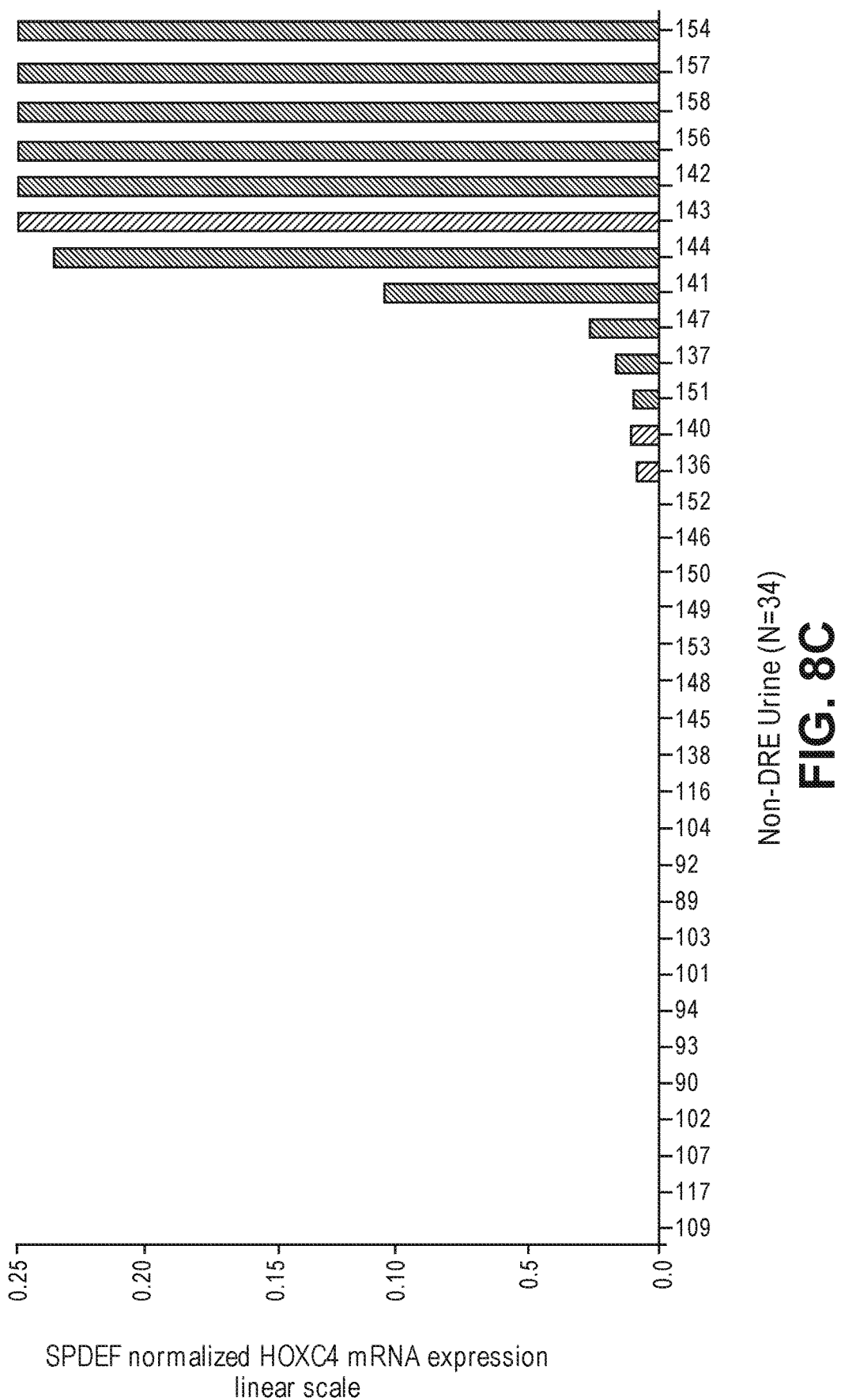

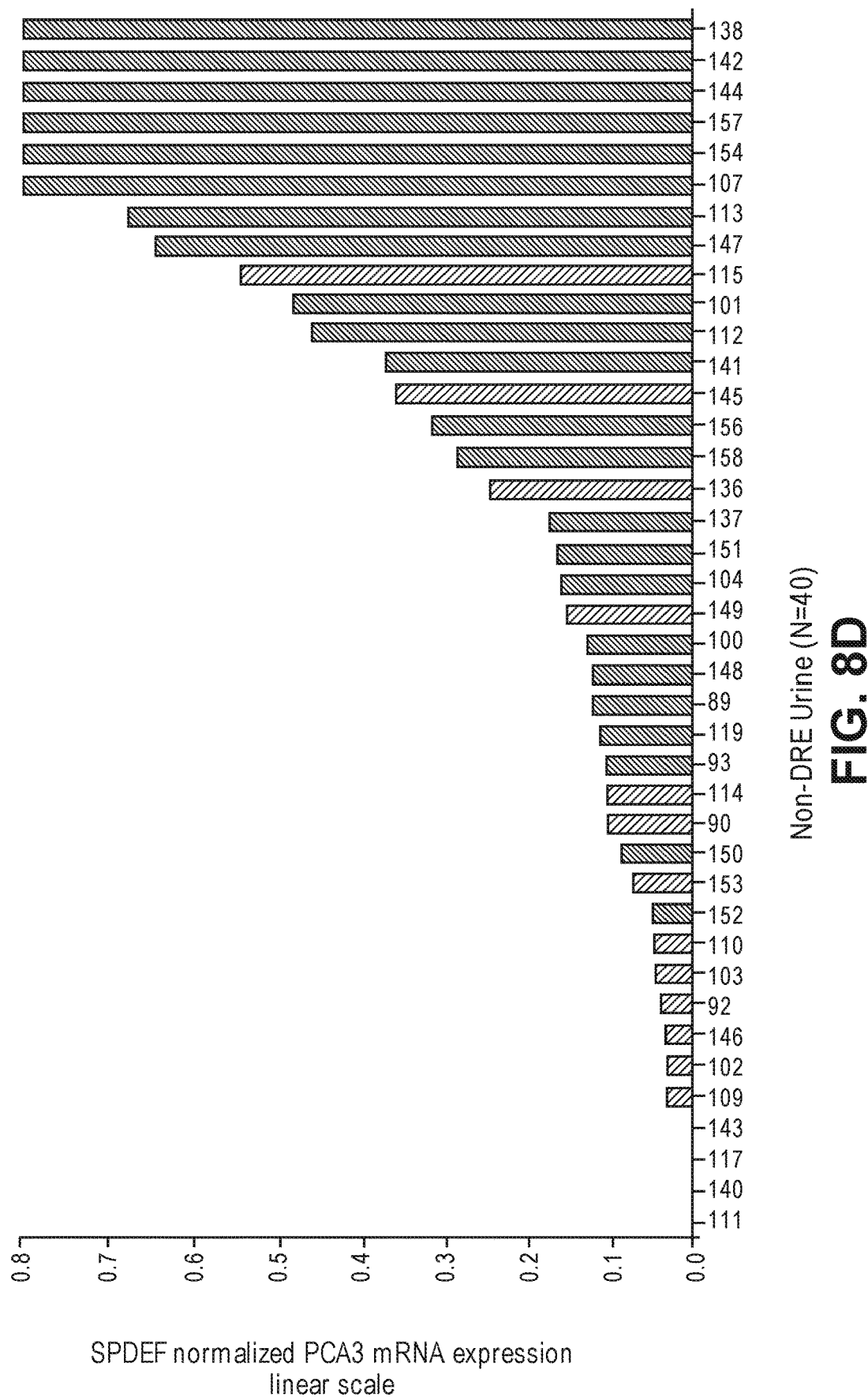

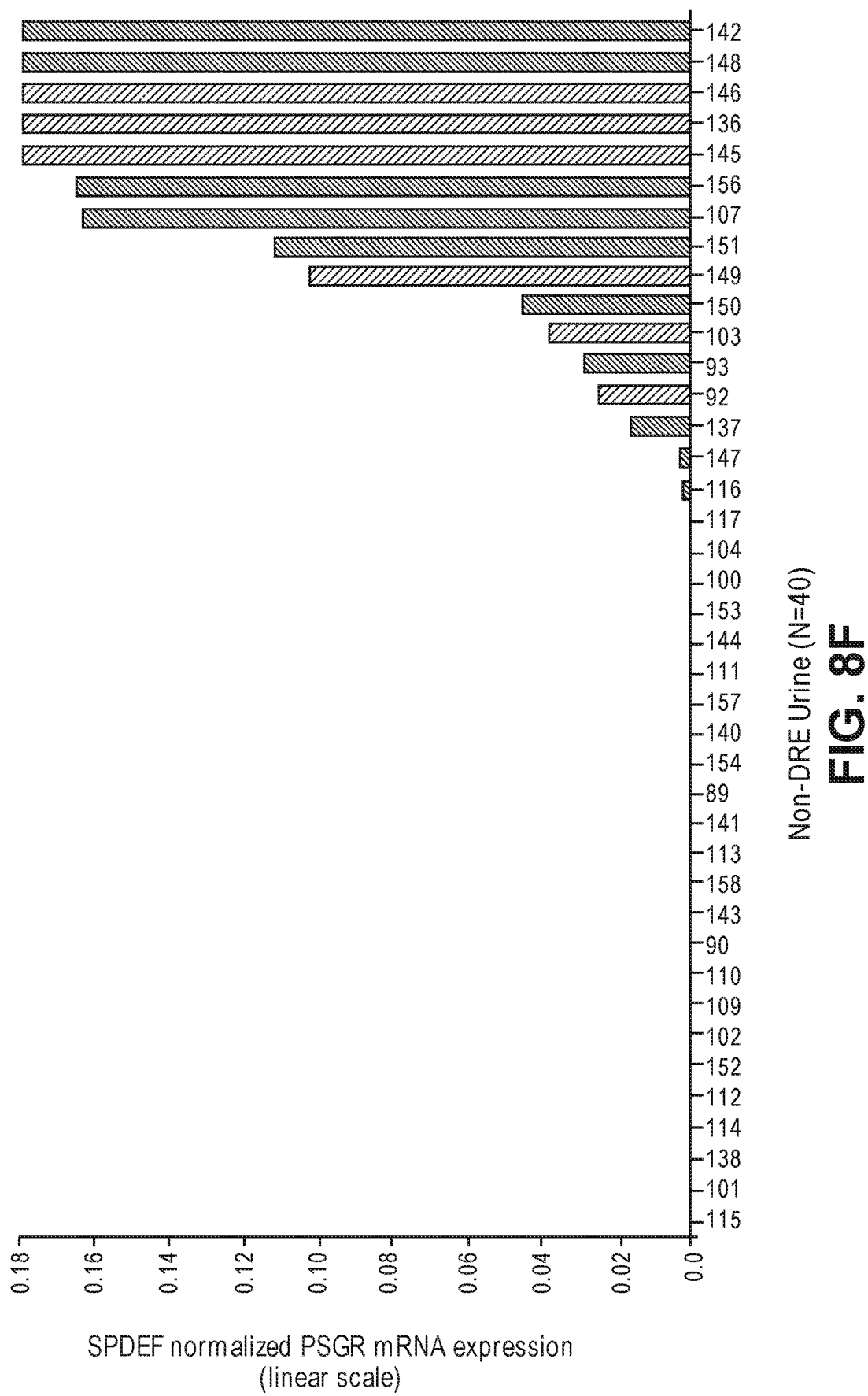

PROSTATE CANCER GENE PROFILES AND METHODS OF USING THE SAME

CROSS-REFERENCE TO RELATED APPLICATIONS

This application is a U.S. National Stage application of PCT/US2018/031550 filed 8 May 2018, which claims priority to U.S. Provisional Patent Application No. 62/505,798 entitled "PROSTATE CANCER GENE PROFILES AND METHODS OF USING THE SAME," filed on May 12, 2017, the entire contents of which are incorporated herein by reference in its entirety.

GOVERNMENT INTEREST

This invention was made with government support under grant ACN 12011-001-0 awarded by the National Institutes of Health/Early Detection Research Network; grant HU0001-10-2-0002 awarded by Uniformed Services University; and grant CA162383-05 awarded by National Institutes of Health's National Cancer Institute RO1 program. The government has certain rights in the invention.

BACKGROUND

Prostate cancer is the second leading cause of cancer death among men in the United States, with an anticipated 180,890 newly diagnosed cases and approximately 26,120 deaths in 2016. It is estimated that 1 in 6 men of African ancestry will be diagnosed with cancer of the prostate (CaP) in their lifetime, in comparison with 1 in 8 men of Caucasian ancestry. Emerging data support biological and genetic differences between African-American (AA) and Caucasian-American (CA) CaP. Tumor sequencing studies have highlighted frequent alterations of ERG, PTEN, and SPOP genes in early stages of CaP, and of the androgen receptor (AR), p53, PIK3CB, and other genes in metastatic CaP or castration resistant prostate cancer. The majority of these studies were performed in men of European ancestry. ERG oncogenic fusion and PTEN deletion are found to be more frequent in CA than AA, while recurrent deletions in LSAMP locus was more prevalent in AA than CA CaP. The lower frequency of overexpression of the key biomarkers (ERG, PCA3) in other ethnic groups, including AA CaP patients, has recently been highlighted.

In clinical practice, early detection of CaP is performed by serum prostate specific antigen (PSA) testing and digital rectal examination (DRE). Serum PSA has remarkably increased CaP detection, but the test exhibits low specificity and low positive predictive value, resulting in high negative biopsy rate and overtreatment. Elevated PSA levels can be detected in men with benign prostatic hyperplasia and prostatitis.

Alternatively, biomarker testing in urine has been found to be an alternative non-invasive screening tool. PCA3 and ERG have been identified as prostate cancer specific biomarkers in urine. However, most of the studies are based on CA cohorts and post-DRE urine specimen.

Therefore, new biomarkers and therapeutic markers that are specific for distinct ethnic populations (e.g., African or Caucasian descent) and provide more accurate diagnostic and/or prognostic potential are needed. Alternatively, combined gene expression profiles are needed that can be used to diagnose or prognose CaP in patients of either African or Caucasian descent, so that similar sensitivity/specificity of cancer detection can be achieved in the two groups using the same set of biomarkers.

SUMMARY

The present disclosure provides gene expression profiles that are associated with prostate cancer and methods of using the same. The gene expression profiles can be used to detect prostate cancer cells in a sample or to predict the likelihood of a patient developing prostate cancer. The gene expression profiles can be measured at either the nucleic acid or protein level. In one aspect, the gene expression profile is specific for patients of African descent. In another aspect, the gene expression profile provides similar sensitivity/specificity of cancer detection in patients of both African and Caucasian descent.

Accordingly, one aspect is directed to a gene expression profile that is associated with prostate cancer and can be used for the sensitive and specific detection of CaP in any patient of interest, including patients of African descent and patients of Caucasian descent. In this aspect, the gene expression profile comprises at least 6, 7, 8, 9, or 10 of the following genes: NKX2-3, DLX1, HOXC4, HOXC6, PSGR, PCA3 (aka DD3), PCGEM1, ERG, COL10A1, and CTBP1. In one embodiment, the gene expression profile comprises all 10 of the aforementioned genes. In one embodiment, the gene expression profile comprises the following six genes: DLX1, NKX2-3, COL10A1, HOXC4, PSGR, and HOXC6, and in one embodiment, the gene expression profile comprises the following six genes: PSGR, DLX1, HOXC4, NKX2-3, PCA3, and ERG. In certain embodiments, one or more genes are used as controls for normalizing expression of the tested genes. In one embodiment, PSA and/or SPDEF is used as the control gene to normalize expression.

Another aspect is directed to a gene expression profile that is associated with prostate cancer in a patient of African descent where the gene expression profile comprises the following genes: PCA3, PCGEM1, and PSGR.

Disclosed herein is a method of obtaining a gene expression profile in a biological sample from a patient comprising detecting expression of a plurality of genes in a biological sample obtained from the patient, wherein the plurality of genes comprises at least six of the following genes: NKX2-3, DLX1, HOXC4, HOXC6, PSGR, PCA3, PCGEM1, ERG, COL10A1, and CTBP1. In one embodiment, the plurality of genes comprises the following six genes: DLX1, NKX2-3, COL10A1, HOXC4, PSGR, and HOXC6. In one embodiment, the plurality of genes comprises the following six genes: PSGR, DLX1, HOXC4, NKX2-3, PCA3, and ERG. In certain embodiments, the plurality of genes comprises the following ten genes: NKX2-3, DLX1, HOXC4, HOXC6, PSGR, PCA3, PCGEM1, ERG, COL10A1, and CTBP1.

Another aspect is directed to a method of obtaining a gene expression profile that is associated with prostate cancer in a patient of African descent, comprising detecting expression of a plurality of genes in a biological sample obtained from the patient, wherein the plurality of genes comprises at least the following genes: PCA3, PCGEM1, and PSGR.

According to certain embodiments, the method of obtaining a gene expression profile further comprises a step of determining if the biological sample contains prostate cancer using the expression data obtained by the detecting step, and in certain embodiments, overexpression of 1) at least one of the following genes: PCA3, PCGEM1, and PSGR; 2) at least one of the following genes: DLX1, NKX2-3, COL10A1, HOXC4, PSGR, and HOXC6; 3) at least one of the following genes: PSGR, DLX1, HOXC4, NKX2-3, PCA3, and ERG; or 4) at least one of the following genes: NKX2-3, DLX1, HOXC4, HOXC6, PSGR, PCA3, PCGEM1, ERG, COL10A1, and CTBP1 as compared to a control or a threshold value indicates the presence of prostate cancer in the biological sample.

In certain embodiments of the method of obtaining a gene expression profile disclosed herein, the biological sample is a tissue sample, a cell sample, a blood sample, a serum sample, or a urine sample, such as a urine sample comprising exosomes, and in certain embodiments, the biological sample comprises prostate cells, or nucleic acids or polypeptides isolated from prostate cells or exosomes. According to various embodiments of the method of obtaining a gene expression profile disclosed herein, nucleic acid or polypeptide expression is detected.

In certain embodiments of the method of obtaining a gene expression profile disclosed herein, the biological sample is urine and the method further comprises a step of extracting mRNA from exosomes in the urine sample prior to the step of detecting expression of the plurality of genes. In the certain embodiments, after the step of extracting mRNA from exosomes, the extracted RNA is converted to cDNA and amplified (e.g., using qRT-PCR).

The gene expression profiles disclosed herein can also be used in a method of diagnosing or prognosing prostate cancer in a patient comprising detecting expression of a plurality of genes in a biological sample obtained from the patient, wherein the plurality of genes comprises 1) PCA3, PCGEM1, and PSGR; or 2) at least 6 of the following genes: NKX2-3, DLX1, HOXC4, HOXC6, PSGR, PCA3, PCGEM1, ERG, COL10A1 and CTBP1, wherein overexpression of 1) at least one of the following genes: PCA3, PCGEM1, and PSGR; or 2) at least one of the following genes: NKX2-3, DLX1, HOXC4, HOXC6, PSGR, PCA3, PCGEM1, ERG, COL10A1, and CTBP1 as compared to a control or a threshold value indicates the presence of prostate cancer in the biological sample.

In certain embodiments, the gene expression profile is used in a method of diagnosing or prognosing prostate cancer in a patient comprising detecting expression of a plurality of genes in a biological sample obtained from the patient, wherein the plurality of genes comprises DLX1, NKX2-3, COL10A1, HOXC4, PSGR, and HOXC6, and wherein overexpression of at least one of the following genes: DLX1, NKX2-3, COL10A1, HOXC4, PSGR, and HOXC6, as compared to a control or threshold value, indicates the presence of prostate cancer in the biological sample.

In certain embodiments, the gene expression profile is used in a method of diagnosing or prognosing prostate cancer in a patient comprising detecting expression of a plurality of genes in a biological sample obtained from the patient, wherein the plurality of genes comprises PSGR, DLX1, HOXC4, NKX2-3, PCA3, and ERG, and wherein overexpression of at least one of the following genes: PSGR, DLX1, HOXC4, NKX2-3, PCA3, and ERG, as compared to a control or threshold value, indicates the presence of prostate cancer in the biological sample or an increased risk of developing prostate cancer.

In certain embodiments, the gene expression profile is used in a method of diagnosing or prognosing prostate cancer in a patient comprising detecting expression of a plurality of genes in a biological sample obtained from the patient, wherein the plurality of genes comprises NKX2-3, DLX1, HOXC4, HOXC6, PSGR, PCA3, PCGEM1, ERG, COL10A1 and CTBP1, and wherein overexpression of at least one of the following genes NKX2-3, DLX1, HOXC4, HOXC6, PSGR, PCA3, PCGEM1, ERG, COL10A1 and CTBP1, as compared to a control or threshold value, indicates the presence of prostate cancer in the biological sample.

These gene profiles can be used in a method of collecting data for diagnosing or prognosing prostate cancer, the method comprising measuring the expression of a representative number of genes in one of the disclosed gene profiles, where gene expression is measured in a sample obtained from a patient. The collected gene expression data can be used to predict whether a subject has prostate cancer or will develop prostate cancer or to predict the stage or severity of prostate cancer. The collected gene expression data can also be used to inform decisions about treating or monitoring a patient. Given the identification of these unique gene expression profiles, one of skill in the art can determine which of the identified genes to include in the gene profiling analysis. A representative number of genes may include all of the genes listed in a particular profile or some lesser number, for example, three or four or more of the genes.

Another aspect is directed to kits for use in diagnosing or prognosing prostate cancer. In one embodiment, the kit comprises a plurality of probes for detecting at least 6 of the following genes (or polypeptides encoded by the same): NKX2-3, DLX1, HOXC4, HOXC6, PSGR, PCA3 (aka DD3), PCGEM1, ERG, COL10A1, and CTBP1. In one embodiment, the kit comprises a plurality of probes for detecting all 10 of the aforementioned genes. In one embodiment, the kit comprises a plurality of probes for detecting the following six genes (or polypeptides encoded by the same): DLX1, NKX2-3, COL10A1, HOXC4, PSGR, and HOXC6. In another embodiment, the kit comprises a plurality of probes for detecting the following six genes (or polypeptides encoded by the same): PSGR, DLX1, HOXC4, NKX2-3, PCA3, and ERG.

In one embodiment, the kit is designed for use in diagnosing or prognosing prostate cancer in a patient of African descent and comprises a plurality of probes for detecting the following genes (or polypeptides encoded by the same): PCA3, PCGEM1, and PSGR.

In certain embodiments, the plurality of probes is selected from a plurality of oligonucleotide probes, a plurality of antibodies, or a plurality of polypeptide probes. In other embodiments, the plurality of probes contains probes for no more than 500, 100, 50, 25, 15, 10, or 5 genes (or polypeptides). In one embodiment, the kit further comprises a probe for detecting expression of one or more control genes, including, but not limited to PSA and SPDEF.

In a related aspect, the disclosure provides an array for diagnosing and/or prognosing prostate cancer. In one embodiment, the array comprises (a) a substrate and (b) a plurality of probes immobilized on the substrate for detecting the expression of at least 6 of the following human genes: NKX2-3, DLX1, HOXC4, HOXC6, PSGR, PCA3 (aka DD3), PCGEM1, ERG, COL10A1, and CTBP1. In one embodiment, the array comprises a plurality of probes immobilized on the substrate for detecting the expression of all 10 of the aforementioned genes. In one embodiment, the array comprises a plurality of probes immobilized on the substrate for detecting the expression of the following six genes: DLX1, NKX2-3, COL10A1, HOXC4, PSGR, and HOXC6. In another embodiment, the array comprises a plurality of probes immobilized on a substrate for detecting the expression of the following six genes: PSGR, DLX1, HOXC4, NKX2-3, PCA3, and ERG. In certain embodiments, the array further comprises probes for detecting expression of one or more control genes, including, but not limited to PSA and SPDEF.

In another embodiment, the array comprises (a) a substrate and (b) a plurality of probes immobilized on the substrate for detecting the expression of the following human genes: PCA3, PCGEM1, and PSGR. In certain embodiments, the array further comprises probes for detecting expression of one or more control genes, including, but not limited to PSA and SPDEF.

The probes on the arrays described herein may be arranged on the substrate within addressable elements to facilitate detection. Typically, the array comprises a limited number of addressable elements so as to distinguish the array from a more comprehensive array, such as a genomic array or the like. Thus, in one embodiment, the array contains 500 or fewer addressable elements. In another embodiment, the array contains no more than 250, 100, 50, 25, 20, 15, 14, 13, 12, 11, 10, 9, 8, 7, 6, 5, 4, or 3 addressable elements. In another embodiment, polynucleotide probes for no more than 50, 25, 20, 15, 10, or 8 genes are immobilized on the array. In another aspect, the disclosure provides methods of using the arrays described herein to detect gene expression in a biological sample. Using these arrays to detect gene expression can also be part of a method for detecting or prognosing prostate cancer in a biological sample.

In another aspect, the disclosure provides methods of using the gene expression profiles described herein to identify a patient in need of prostate cancer treatment. The methods can also further comprise a step of treating a patient who has been identified as needing prostate cancer treatment.

BRIEF DESCRIPTION OF THE DRAWINGS

The accompanying drawings, which are included to provide a further understanding of the disclosure, are incorporated in and constitute a part of this specification. The drawings illustrate embodiments of the disclosure and, together with the detailed description, serve to explain the principles of the disclosure. No attempt is made to show structural details of the disclosure in more detail than may be necessary for a fundamental understanding of the disclosure and various ways in which it may be practiced.

FIG. 7B is a bar graph showing SPDEF-normalized mRNA expression for ERG in 91 non-DRE urinary exosome-based patient specimens, where solid shaded bars indicate a positive biopsy, striped bars indicate a negative biopsy, and dotted bars indicate unknown biopsy status.

FIG. 8A is a bar graph showing SPDEF-normalized mRNA expression for DLX1 in 40 non-DRE urinary exosome-based patient specimens, where narrow stripes indicate a positive biopsy and broad stripes indicate a negative biopsy.

FIG. 8C is a bar graph showing SPDEF-normalized mRNA expression for HOXC4 in 34 non-DRE urinary exosome-based patient specimens, where narrow stripes indicate a positive biopsy and broad stripes indicate a negative biopsy.

FIG. 8D is a bar graph showing SPDEF-normalized mRNA expression for PCA3 in 40 non-DRE urinary exosome-based patient specimens, where narrow stripes indicate a positive biopsy and broad stripes indicate a negative biopsy.

FIG. 8F is a bar graph showing SPDEF-normalized mRNA expression for PSGR in 40 non-DRE urinary exosome-based patient specimens, where narrow stripes indicate a positive biopsy and broad stripes indicate a negative biopsy.

Figure 1:
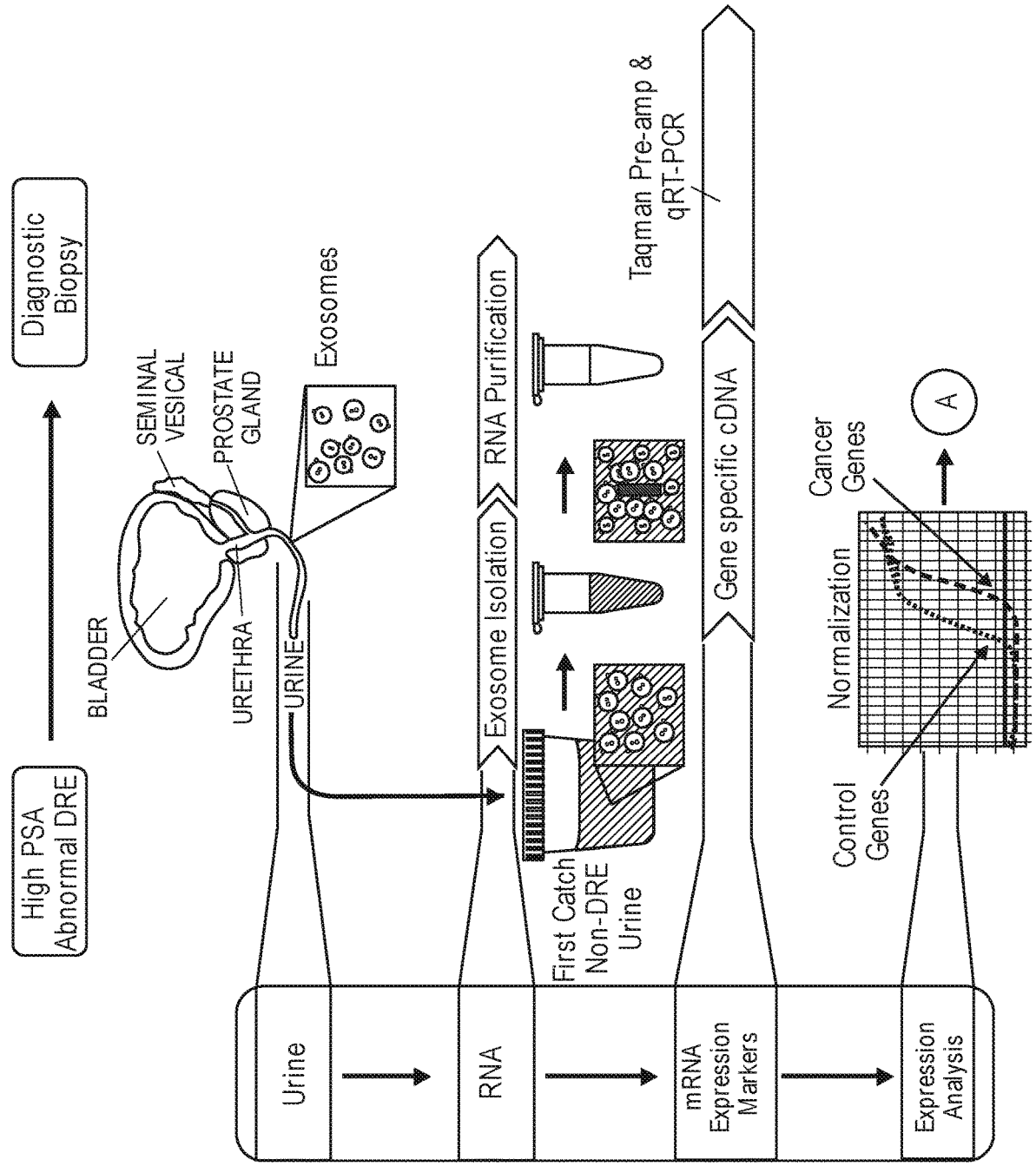
FIG. 1 is a schematic illustration showing a non-limiting assay work flow in a patient urine-derived exosome specimen.
Figure 1:
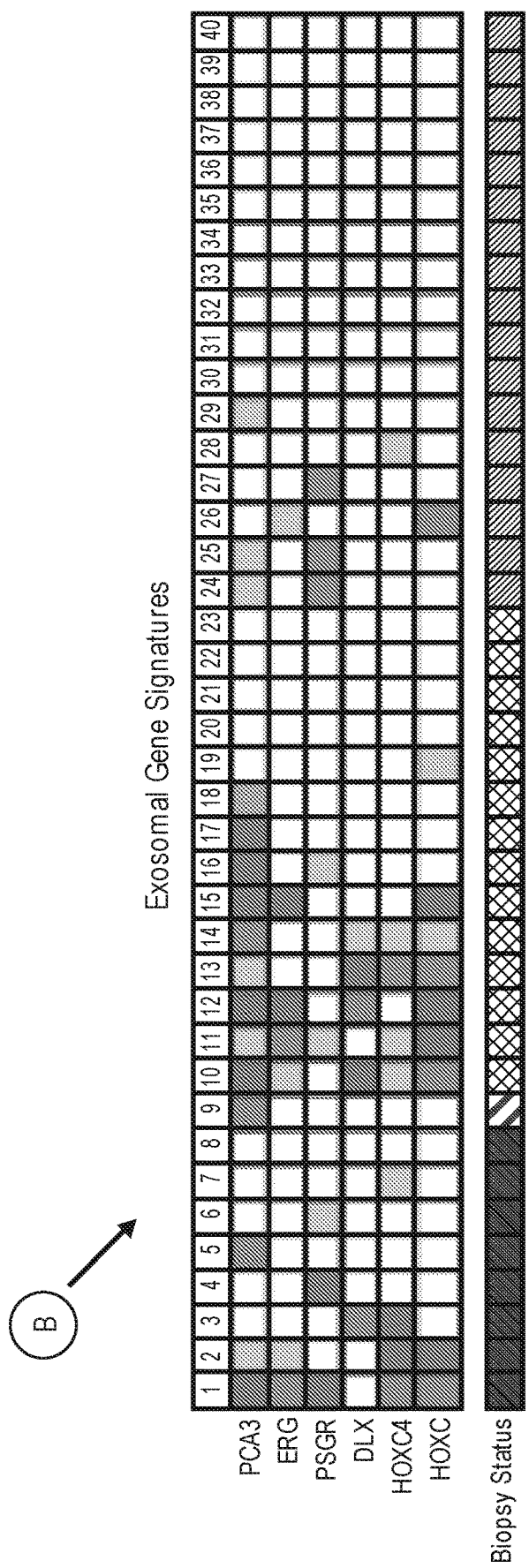
Figure 2A:
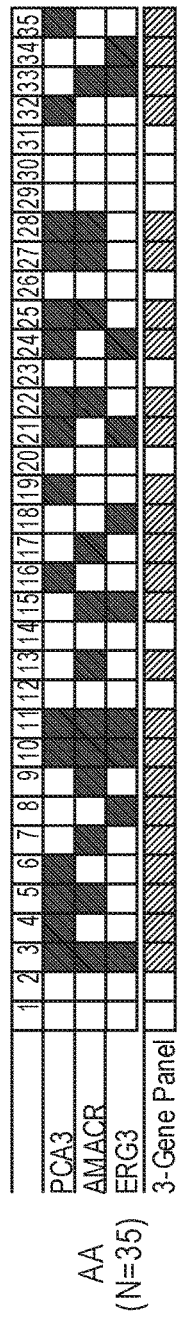
FIG. 2A is a heatmap displaying mRNA expression levels assessed by qRT-PCR for three selected genes (PCA, AMACR, and ERG3) in laser capture micro-dissected matched tumor-normal prostate tissue of 35 AA patients.
Figure 2B:
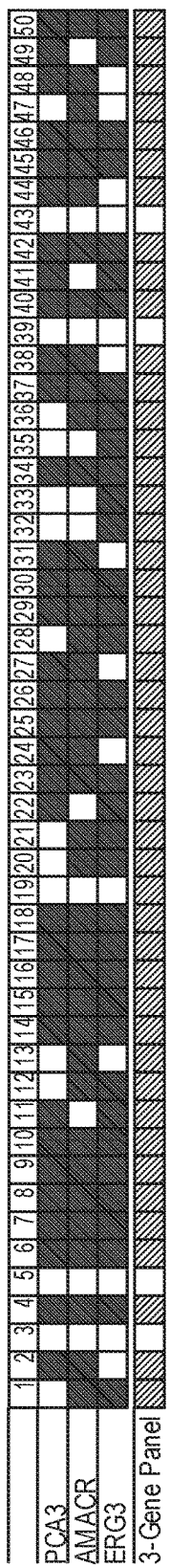
FIG. 2B is a heatmap displaying mRNA expression levels assessed by qRT-PCR for three selected genes (PCA, AMACR, and ERG3) in laser capture micro-dissected matched tumor-normal prostate tissue of 50 CA patients.
Figure 2C:
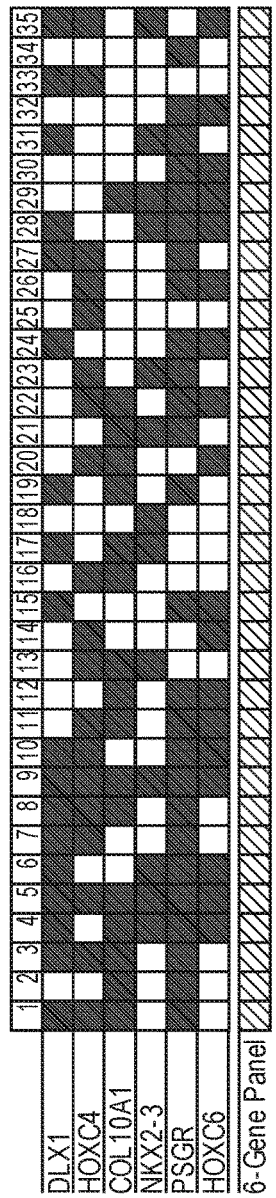
FIG. 2C is a heatmap displaying mRNA expression levels assessed by qRT-PCR for six selected genes (DLX1, HOXC4, COL10A1, NKX2-3, PSGR, and HOXC6) in laser capture micro-dissected matched tumor-normal prostate tissue of 35 AA patients.
Figure 2D:
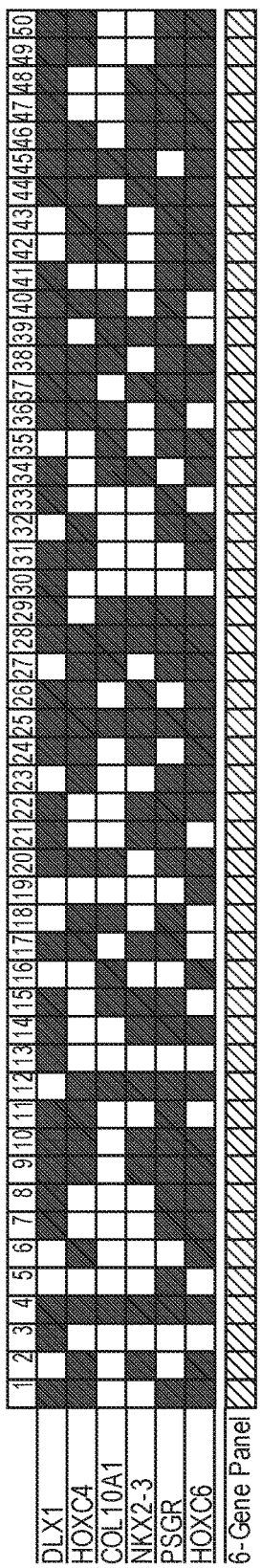
FIG. 2D is a heatmap displaying mRNA expression levels assessed by qRT-PCR for six selected genes (DLX1, HOXC4, COL10A1, NKX2-3, PSGR, and HOXC6) in laser capture micro-dissected matched tumor-normal prostate tissue of 50 CA patients.

The drawings are not necessarily to scale, and may, in part, include exaggerated dimensions for clarity.

DETAILED DESCRIPTION

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "of African descent" refers to individuals who self-identify as being of African descent, including individuals who self-identify as being African-American, and individuals determined to have genetic markers correlated with African ancestry, also called Ancestry Informative Markers (AIM), such as the AIMs identified in Judith Kidd et al., *Analyses of a set of 128 ancestry informative single-nucleotide polymorphisms in a global set of 119 population samples*, INVESTIGATIVE GENETICS, (2):1, 2011, which reference is incorporated by reference in its entirety.

The term "of Caucasian descent" refers to individuals who self-identify as being of Caucasian descent, including individuals who self-identify as being Caucasian-American, and individuals determined to have genetic markers correlated with Caucasian ancestry, such as European, North African, or Asian (Western, Central or Southern) ancestry, also called Ancestry Informative Markers (AIM), such as the AIMs identified in Judith Kidd et al., *Analyses of a set of 128 ancestry informative single-nucleotide polymorphisms in a global set of 119 population samples*, INVESTIGATIVE GENETICS, (2):1, 2011, which reference is incorporated by reference in its entirety.

The term "antibody" refers to an immunoglobulin or antigen-binding fragment thereof, and encompasses any polypeptide comprising an antigen-binding fragment or an antigen-binding domain. The term includes but is not limited to polyclonal, monoclonal, monospecific, polyspecific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')2, Fv, scFv, Fd, dAb, and other antibody fragments that retain antigen-binding function. Unless otherwise specified, an antibody is not necessarily from any particular source, nor is it produced by any particular method.

The term "detecting" or "detection" means any of a variety of methods known in the art for determining the presence or amount of a nucleic acid or a protein. As used throughout the specification, the term "detecting" or "detection" includes either qualitative or quantitative detection.

The term "gene expression profile" refers to the expression levels of a plurality of genes in a sample. As is understood in the art, the expression level of a gene can be analyzed by measuring the expression of a nucleic acid (e.g., genomic DNA or mRNA) or a polypeptide that is encoded by the nucleic acid.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived.

The terms "polypeptide," "peptide," and "protein" are used interchangeably herein to refer to polymers of amino acids.

The term "polypeptide probe" as used herein refers to a labeled (e.g., isotopically labeled) polypeptide that can be used in a protein detection assay (e.g., mass spectrometry) to quantify a polypeptide of interest in a biological sample.

The term "primer" means a polynucleotide capable of binding to a region of a target nucleic acid, or its complement, and promoting nucleic acid amplification of the target nucleic acid. Generally, a primer will have a free 3' end that can be extended by a nucleic acid polymerase. Primers also generally include a base sequence capable of hybridizing via complementary base interactions either directly with at least one strand of the target nucleic acid or with a strand that is complementary to the target sequence. A primer may comprise target-specific sequences and optionally other sequences that are non-complementary to the target sequence. These non-complementary sequences may comprise, for example, a promoter sequence or a restriction endonuclease recognition site.

A "variation" or "variant" refers to an allele sequence that is different from the reference at as little as a single base or for a longer interval.

The term "ERG" or "ERG gene" refers to Ets-related gene (ERG), which has been assigned the unique Hugo Gene Nomenclature Committee (HGNC) identifier code: HGNC: 3446, and includes ERG gene fusion products that are prevalent in prostate cancer, including TMPRSS2-ERG fusion products. Analyzing the expression of ERG or the ERG gene includes analyzing the expression of ERG gene fusion products that are associated with prostate cancer, such as TMPRSS2-ERG.

Detecting Gene Expression

As used herein, measuring or detecting the expression of any of the foregoing genes or nucleic acids comprises measuring or detecting any nucleic acid transcript (e.g., mRNA, cDNA, or genomic DNA) corresponding to the gene of interest or the protein encoded thereby. If a gene is associated with more than one mRNA transcript or isoform, the expression of the gene can be measured or detected by measuring or detecting one or more of the mRNA transcripts of the gene, or all of the mRNA transcripts associated with the gene.

Typically, gene expression can be detected or measured on the basis of mRNA or cDNA levels, although protein levels also can be used when appropriate. Any quantitative or qualitative method for measuring mRNA levels, cDNA, or protein levels can be used. Suitable methods of detecting or measuring mRNA or cDNA levels include, for example, Northern Blotting, microarray analysis, or a nucleic acid amplification procedure, such as reverse-transcription PCR (RT-PCR) or real-time RT-PCR, also known as quantitative RT-PCR (qRT-PCR). Such methods are well known in the art. See e.g., Sambrook et al., Molecular Cloning: A Laboratory Manual, 4$^{th}$ Ed., Cold Spring Harbor Press, Cold Spring Harbor, N.Y., 2012. Other techniques include digital, multiplexed analysis of gene expression, such as the nCounter® (NanoString Technologies, Seattle, WA) gene expression assays, which are further described in US20100112710 and US20100047924.

Detecting a nucleic acid of interest generally involves hybridization between a target (e.g. mRNA, cDNA, or genomic DNA) and a probe. Sequences of the genes used in the prostate cancer gene expression profile are known. Therefore, one of skill in the art can readily design hybridization probes for detecting those genes. See, e.g., Sambrook et al., Molecular Cloning: A Laboratory Manual, 4$^{th}$ Ed., Cold Spring Harbor Press, Cold Spring Harbor, N.Y., 2012. Each probe may be substantially specific for its target, to avoid any cross-hybridization and false positives. An alternative to using specific probes is to use specific reagents when deriving materials from transcripts (e.g., during cDNA production, or using target-specific primers during amplification). In both cases specificity can be achieved by hybridization to portions of the targets that are substantially unique within the group of genes being analyzed, for example hybridization to the polyA tail would not provide specificity. If a target has multiple splice variants, it is possible to design a hybridization reagent that recognizes a region common to each variant and/or to use more than one reagent, each of which may recognize one or more variants.

In certain embodiments, microarray analysis or a PCR-based method is used. In this respect, measuring the expression of the foregoing nucleic acids in a biological sample can comprise, for instance, contacting a sample containing or suspected of containing prostate cancer cells or exosomes derived therefrom with polynucleotide probes specific to the genes of interest, or with primers designed to amplify a portion of the genes of interest, and detecting binding of the probes to the nucleic acid targets or amplification of the nucleic acids, respectively. Detailed protocols for designing PCR primers are known in the art. See e.g., Sambrook et al., Molecular Cloning: A Laboratory Manual, 4$^{th}$ Ed., Cold Spring Harbor Press, Cold Spring Harbor, N.Y., 2012. Similarly, detailed protocols for preparing and using microarrays to analyze gene expression are known in the art and described herein.

Alternatively or additionally, expression levels of genes can be determined at the protein level, meaning that levels of proteins encoded by the genes discussed herein are measured. Several methods and devices are known for determining levels of proteins including immunoassays, such as described, for example, in U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; 5,458,852; and 5,480,792, each of which is hereby incorporated by reference in its entirety. These assays may include various sandwich, competitive, or non-competitive assay formats, to generate a signal that is related to the presence or amount of a protein of interest. Any suitable immunoassay may be utilized, for example, lateral flow, enzyme-linked immunoassays (ELISA), radioimmunoassays (RIAs), competitive binding assays, and the like. Numerous formats for antibody arrays have been described. Such arrays may include different antibodies having specificity for different proteins intended to be detected. For example, at least 100 different antibodies are used to detect 100 different protein targets, each antibody being specific for one target. Other ligands having specificity for a particular protein target can also be used, such as the synthetic antibodies disclosed in WO 2008/048970, which is hereby incorporated by reference in its entirety. Other compounds with a desired binding specificity can be selected from random libraries of peptides or small molecules. U.S. Pat. No. 5,922,615, which is hereby incorporated by reference in its entirety, describes a device that uses multiple discrete zones of immobilized antibodies on membranes to detect multiple target antigens in an array. Microtiter plates or automation can be used to facilitate detection of large numbers of different proteins.

One type of immunoassay, called nucleic acid detection immunoassay (NADIA), combines the specificity of protein antigen detection by immunoassay with the sensitivity and precision of the polymerase chain reaction (PCR). This amplified DNA-immunoassay approach is similar to that of an enzyme immunoassay, involving antibody binding reactions and intermediate washing steps, except the enzyme label is replaced by a strand of DNA and detected by an amplification reaction using an amplification technique, such as PCR. Exemplary NADIA techniques are described in U.S. Pat. No. 5,665,539 and published U.S. Application 2008/0131883, both of which are hereby incorporated by reference in their entirety. Briefly, NADIA uses a first (reporter) antibody that is specific for the protein of interest and labelled with an assay-specific nucleic acid. The presence of the nucleic acid does not interfere with the binding of the antibody, nor does the antibody interfere with the nucleic acid amplification and detection. Typically, a second (capturing) antibody that is specific for a different epitope on the protein of interest is coated onto a solid phase (e.g., paramagnetic particles). The reporter antibody/nucleic acid conjugate is reacted with sample in a microtiter plate to form a first immune complex with the target antigen. The immune complex is then captured onto the solid phase particles coated with the capture antibody, forming an insoluble sandwich immune complex. The microparticles are washed to remove excess, unbound reporter antibody/nucleic acid conjugate. The bound nucleic acid label is then detected by subjecting the suspended particles to an amplification reaction (e.g. PCR) and monitoring the amplified nucleic acid product.

Although immunoassays have been used for the identification and quantification of proteins, recent advances in mass spectrometry (MS) techniques have led to the development of sensitive, high-throughput MS protein analyses. The MS methods can be used to detect low abundant proteins in complex biological samples. For example, it is possible to perform targeted MS by fractionating the biological sample prior to MS analysis. Common techniques for carrying out such fractionation prior to MS analysis include, for example, two-dimensional electrophoresis, liquid chromatography, and capillary electrophoresis. Selected reaction monitoring (SRM), also known as multiple reaction monitoring (MRM), has also emerged as a useful high-throughput MS-based technique for quantifying targeted proteins in complex biological samples, including prostate cancer biomarkers that are encoded by gene fusions (e.g., TMPRSS2/ERG).

Samples

The methods described herein involve analysis of gene expression profiles in prostate cells or exosomes derived therefrom. These prostate cells or exosomes may be found in a biological sample, such as prostate tissue, blood, serum, plasma, urine, saliva, or prostatic fluid. Nucleic acids or polypeptides may be isolated from the cells or exosomes prior to detecting gene expression.

In one embodiment, the biological sample comprises prostate tissue and is obtained through a biopsy, such as a transrectal or transperineal biopsy. In another embodiment, the biological sample is urine. Urine samples may be collected following a digital rectal examination (DRE) or a prostate biopsy. Alternatively, urine samples may be collected in regular urine specimens without a DRE or prostate biopsy ("non-DRE urine sample"). In another embodiment, the biological sample is blood, serum, or plasma, and contains circulating tumor cells that have detached from a primary tumor.

The sample may also contain tumor-derived exosomes. Exosomes are small (such as from about 30 nm to about 100 nm) membrane-bound particles that are released from normal, diseased, and neoplastic cells and are present in blood and urine and other bodily fluids. In certain embodiments, the sample is a urine sample, such as a non-DRE urine sample, that contains exosomes. The methods disclosed herein can be used with biological samples collected from a variety of mammals, and in certain embodiments, the methods disclosed herein may be used with biological samples obtained from a human subject.

In certain embodiments, exosomes from biological samples, such as urine samples including non-DRE urine samples, may be isolated and their RNA extracted for gene specific expression analysis, as illustrated schematically in FIG. 1. Exosome mRNA may be extracted from urine samples by any means known in the art, such as with a commercially-available exosome RNA isolation kit, for example the Urine Exosome RNA Isolation Kit (Norgen Biotek Corp.; Cat. 47200) or as disclosed in US20160177401, which is hereby incorporated by reference in its entirety. After extraction, exosome RNA may be purified for further analysis, such as analysis for gene expression.

In certain embodiments, RNA obtained from exosomes may be subjected to qRT-PCR. Reverse transcription may occur by any methods known in the art, such as through the use of an Omniscript RT Kit (Qiagen). In certain embodiments, the reverse transcription may use reverse primers, such as gene specific primer (GSP) pool of custom designed reverse primers. The resultant cDNA may then be amplified by any amplification technique known in the art. In certain embodiments, the cDNA is amplified using a polymerase chain reaction. Gene expression may then be analyzed through the use of, for example, control genes described below. As described herein, the over- or underexpression of genes relative to control genes may be measured to determine an exosomal gene expression profile for an individual urine sample. FIG. 1 schematically illustrates a non-limiting process for obtaining an exosomal gene expression profile from a urine sample comprising exosomes.

Controls

In certain embodiments, the control may be any suitable reference that allows evaluation of the expression level of the genes in the prostate cancer cells or exosomes as compared to the expression of the same genes in a sample comprising non-cancerous prostate cells, such as normal prostate epithelial cells (or exosomes derived therefrom) from a matched subject, or a pool of such samples. Thus, for instance, the control can be a sample from the same subject that is analyzed simultaneously or sequentially with the test sample, or the control can be the average expression level of the genes of interest in a pool of prostate samples known to be non-cancerous. Alternatively, the control can be defined by mRNA copy numbers of other genes in the sample, such as housekeeping genes (e.g., PBGD or GAPDH) or other genes (e.g., PSA or SPDEF) that can be used to normalize gene expression levels. In certain embodiments, the control gene is PSA and/or SPDEF. In certain embodiments, the control is a predetermined "cut-off" or threshold value of absolute expression. Thus, the control can be embodied, for example, in a pre-prepared microarray used as a standard or reference, or in data that reflects the expression profile of relevant genes in a sample or pool of non-cancerous samples, such as might be part of an electronic database or computer program.

Overexpression and decreased expression of a gene can be determined by any suitable method, such as by comparing the expression of the genes in a test sample with a control (e.g., a positive or negative control or threshold value). A control can be provided as previously discussed. Regardless of the method used, overexpression and decreased expression can be defined as any level of expression greater than or less than the level of expression of a control gene or threshold value. By way of further illustration, overexpression can be defined as expression that is at least about 1.2-fold, 1.5-fold, 2-fold, 2.5-fold, 4-fold, 5-fold, 10-fold, 20-fold, 50-fold, 100-fold higher or even greater expression as compared to tissue control gene or threshold value, and decreased expression can similarly be defined as expression that is at least about 1.2-fold, 1.5-fold, 2-fold, 2.5-fold, 4-fold, 5-fold, 10-fold, 20-fold, 50-fold, 100-fold lower or even lower expression as compared to tissue control gene or threshold value. In one embodiment, overexpression or decreased expression as used herein is defined as expression that is at least about 4-fold higher or lower, respectively, as compared to a control gene or threshold value.

Prostate Cancer

This disclosure provides gene expression profiles that are associated with prostate cancer. The gene expression profiles can be used to detect prostate cancer cells in a sample.

When prostate cancer is found in a biopsy, it may be graded to estimate how quickly it is likely to grow and spread. The most commonly used prostate cancer grading system, called Gleason grading, evaluates prostate cancer cells on a scale of 1 to 5, based on their pattern when viewed under a microscope.

Cancer cells that still resemble healthy prostate cells have uniform patterns with well-defined boundaries and are considered well-differentiated (Gleason grades 1 and 2). The more closely the cancer cells resemble prostate tissue, the more the cells will behave like normal prostate tissue and the less aggressive the cancer. Gleason grade 3, the most common grade, shows cells that are moderately differentiated, that is, still somewhat well-differentiated, but with boundaries that are not as well-defined. Poorly-differentiated cancer cells have random patterns with poorly defined boundaries and no longer resemble prostate tissue (Gleason grades 4 and 5), indicating a more aggressive cancer.

Prostate cancers often have areas with different grades. A combined Gleason score is determined by adding the grades from the two most common cancer cell patterns within the tumor. For example, if the most common pattern is grade 4 and the second most common pattern is grade 3, then the combined Gleason score is 4+3=7. If there is only one pattern within the tumor, the combined Gleason score can be as low as 1+1=2 or as high as 5+5=10. Combined scores of 2 to 4 are considered well-differentiated, scores of 5 to 6 are considered moderately-differentiated and scores of 7 to 10 are considered poorly-differentiated. Cancers with a high Gleason score are more likely to have already spread beyond the prostate gland at the time they were found.

In general, the lower the Gleason score, the less aggressive the cancer and the better the prognosis (outlook for cure or long-term survival). The higher the Gleason score, the more aggressive the cancer and the poorer the prognosis for long-term, metastasis-free survival.

Arrays

A convenient way of measuring RNA transcript levels for multiple genes in parallel is to use an array (also referred to as microarrays in the art). Techniques for using arrays to assess and compare gene expression levels are well-known in the art and include appropriate hybridization, detection and data processing protocols. A useful array may include multiple polynucleotide probes (such as DNA) that are immobilized on a solid substrate (e.g., a glass support such as a microscope slide, or a membrane) in separate locations (e.g., addressable elements) such that detectable hybridization can occur between the probes and the transcripts to indicate the amount of each transcript that is present. The arrays disclosed herein can be used in methods of detecting the expression of a desired combination of genes, which combinations are discussed herein.

In one embodiment, the array comprises (a) a substrate and (b) at least 6 different addressable elements that each comprise at least one polynucleotide probe for detecting the expression of an mRNA transcript (or cDNA synthesized from the mRNA transcript) of one of the following human genes: NKX2-3, DLX1, HOXC4, HOXC6, PSGR, PCA3 (aka DD3), PCGEM1, ERG, COL10A1, and CTBP1. In one embodiment, the substrate comprises 6 different addressable elements, wherein each different addressable element is specific for one of the following human genes: DLX1, NKX2-3, COL10A1, HOXC4, PSGR, and HOXC6, such that the array can be used to simultaneously detect the expression of these 6 genes. In another embodiment, the substrate comprises 6 different addressable elements, wherein each different addressable element is specific for one of the following human genes: PSGR, DLX1, HOXC4, NKX2-3, PCA3, and ERG, such that the array can be used to simultaneously detect the expression of these 6 genes. In one embodiment, the substrate comprises 10 different addressable elements, wherein each different addressable element is specific for one of the following human genes: NKX2-3, DLX1, HOXC4, HOXC6, PSGR, PCA3 (aka DD3), PCGEM1, ERG, COL10A1, and CTBP1, such that the array can be used to simultaneously detect the expression of these 10 genes. In certain embodiments, the array further comprises one or more different addressable elements comprising at least one oligonucleotide probe for detecting the expression of an mRNA transcript (or cDNA synthesized from the mRNA transcript) of a control gene. In certain embodiments, the control gene is PSA and/or SPDEF.

In another embodiment, the array comprises (a) a substrate and (b) 3 or more different addressable elements that each comprise at least one polynucleotide probe for detecting the expression of an mRNA transcript (or cDNA synthesized from the mRNA transcript) of the following human genes: PCA3, PCGEM1, and PSGR. In certain embodiments, the array further comprises one or more different addressable elements comprising at least one oligonucleotide probe for detecting the expression of an mRNA transcript (or cDNA synthesized from the mRNA transcript) of one or more control genes, such as PSA and/or SPDEF.

As used herein, the term "addressable element" means an element that is attached to the substrate at a predetermined position and specifically binds a known target molecule, such that when target-binding is detected (e.g., by fluorescent labeling), information regarding the identity of the bound molecule is provided on the basis of the location of the element on the substrate. Addressable elements are "different" for the purposes of the present disclosure if they do not bind to the same target gene. The addressable element comprises one or more polynucleotide probes specific for an mRNA transcript of a given gene, or a cDNA synthesized from the mRNA transcript. The addressable element can comprise more than one copy of a polynucleotide or can comprise more than one different polynucleotide, provided that all of the polynucleotides bind the same target molecule. Where a gene is known to express more than one mRNA transcript, the addressable element for the gene can comprise different probes for different transcripts, or probes designed to detect a nucleic acid sequence common to two or more (or all) of the transcripts. Alternatively, the array can comprise an addressable element for the different transcripts. The addressable element also can comprise a detectable label, suitable examples of which are well known in the art.

The array can comprise addressable elements that bind to mRNA or cDNA other than that of 1) NKX2-3, DLX1, HOXC4, HOXC6, PSGR, PCA3 (aka DD3), PCGEM1, ERG, COL10A1, and CTBP1; 2) DLX1, NKX2-3, COL10A1, HOXC4, PSGR, and HOXC6; 3) PSGR, DLX1, HOXC4, NKX2-3, PCA3, and ERG or 4) PCA3, PCGEM1, and PSGR. An array capable of detecting a vast number of targets (e.g., mRNA or polypeptide targets), such as arrays designed for comprehensive expression profiling of a cell line, chromosome, genome, or the like, are not economical or convenient for collecting data to use in diagnosing and/or prognosing prostate cancer. Thus, to facilitate the convenient use of the array as a diagnostic tool or screen, for example, in conjunction with the methods described herein, the array may comprise a limited number of addressable elements. In this regard, in one embodiment, the array comprises no more than about 1000 different addressable elements, such as no more than about 500 different addressable elements, no more than about 250 different addressable elements, or even no more than about 100 different addressable elements, such as about 75 or fewer different addressable elements, or even about 50 or fewer different addressable elements. In certain embodiments, the array contains no more than 25 different addressable elements. In certain embodiments, the array contains no more than 15 different addressable elements. In certain embodiments, the array contains no more than 12 different addressable elements. In certain embodiments, the array contains no more than 8 different addressable elements. In certain embodiments, the array contains no more than 5 different addressable elements.

It is also possible to distinguish these diagnostic arrays from the more comprehensive genomic arrays and the like by limiting the number of polynucleotide probes on the array. Thus, in one embodiment, the array has polynucleotide probes for no more than 1000 genes immobilized on the substrate. In other embodiments, the array has oligonucleotide probes for no more than 500, no more than 250, no more than 100, or no more than 50 genes. In certain embodiments, the array has oligonucleotide probes for no more than 25 genes. In certain embodiments, the array has oligonucleotide probes for no more than 15 genes. In certain embodiments, the array has oligonucleotide probes for, no more than 12 genes. In certain embodiments, the array has oligonucleotide probes for no more than 8 genes. In certain embodiments, the array has oligonucleotide probes for no more than 5 genes.

The substrate can be any rigid or semi-rigid support to which polynucleotides can be covalently or non-covalently attached. Suitable substrates include membranes, filters, chips, slides, wafers, fibers, beads, gels, capillaries, plates, polymers, microparticles, and the like. Materials that are suitable for substrates include, for example, nylon, glass, ceramic, plastic, silica, aluminosilicates, borosilicates, metal oxides such as alumina and nickel oxide, various clays, nitrocellulose, and the like.

The polynucleotides of the addressable elements (also referred to as "probes") can be attached to the substrate in a pre-determined 1- or 2-dimensional arrangement, such that the pattern of hybridization or binding to a probe is easily correlated with the expression of a particular gene. Because the probes are located at specified locations on the substrate (i.e., the elements are "addressable"), the hybridization or binding patterns and intensities create a unique expression profile, which can be interpreted in terms of expression levels of particular genes and can be correlated with prostate cancer in accordance with the methods described herein.

Polynucleotide and polypeptide probes can be generated by any suitable method known in the art (see e.g., Sambrook et al., Molecular Cloning: A Laboratory Manual, 4$^{th}$ Ed., Cold Spring Harbor Press, Cold Spring Harbor, N.Y., 2012). For example, polynucleotide probes that specifically bind to the mRNA transcripts of the genes described herein (or cDNA synthesized therefrom) can be created using the nucleic acid sequences of the mRNA or cDNA targets themselves by routine techniques (e.g., PCR or synthesis). As used herein, the term "fragment" means a contiguous part or portion of a polynucleotide sequence comprising about 10 or more nucleotides, about 15 or more nucleotides, about 20 or more nucleotides, about 30 or more, or even about 50 or more nucleotides. By way of further illustration, a polynucleotide probe that binds to an mRNA transcript of DLX1 (or cDNA corresponding thereto) can be provided by a polynucleotide comprising a nucleic acid sequence that is complementary to the DLX1 mRNA transcript or a fragment thereof, or sufficiently complementary to the DLX1 mRNA transcript or fragment thereof that it selectively binds to the DLX1 mRNA transcript. The same is true with respect to the other genes described herein. Any probe that will selectively bind the mRNA or cDNA target can be used. In certain embodiments, the polynucleotide probes will comprise 10 or more nucleic acids, 20 or more, 50 or more, or 100 or more nucleic acids. In order to confer sufficient specificity, the probe may have a sequence identity to a complement of the target sequence of about 90% or more, such as about 95% or more (e.g., about 98% or more or about 99% or more) as determined, for example, using the well-known Basic Local Alignment Search Tool (BLAST) algorithm (available through the National Center for Biotechnology Information (NCBI), Bethesda, Md.).

Stringency of hybridization reactions is readily determinable by one of ordinary skill in the art, and generally is an empirical calculation dependent upon probe length, washing temperature, and salt concentration. In general, longer probes may require higher temperatures for proper annealing, while shorter probes may require lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so.

"Stringent conditions" or "high stringency conditions," as defined herein, are identified by, but not limited to, those that: (1) use low ionic strength and high temperature for washing, for example 0.015 M sodium chloride/0.0015 M sodium citrate/0.1% sodium dodecyl sulfate at 50° C.; (2) use during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) use 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The array can comprise other elements common to polynucleotide arrays. For instance, the array also can include one or more elements that serve as a control, standard, or reference molecule, such as a housekeeping gene or portion thereof (e.g., PBGD or GAPDH) or other gene or portion thereof (e.g., PSA, SPDEF), to assist in the normalization of expression levels or the determination of nucleic acid quality and binding characteristics, reagent quality and effectiveness, hybridization success, analysis thresholds and success, etc. These other common aspects of the arrays or the addressable elements, as well as methods for constructing and using arrays, including generating, labeling, and attaching suitable probes to the substrate, consistent with the invention are well-known in the art. Other aspects of the array are as described with respect to the methods disclosed herein.

In one embodiment, the array comprises (a) a substrate and (b) 10 or more different addressable elements that each comprise at least one polynucleotide probe for detecting the expression of an mRNA transcript (or cDNA synthesized from the mRNA transcript) of one of the following human genes: NKX2-3, DLX1, HOXC4, HOXC6, PSGR, PCA3, PCGEM1, ERG, COL10A1, and CTBP1, wherein the array comprises no more than 500, no more than 250, no more than 100, no more than 50, no more than 25, or no more than 15 different addressable elements. In certain embodiments, the array contains no more than 100 different addressable elements. In certain embodiments, the array contains no more than 25 different addressable elements. In certain embodiments, the array contains no more than 15 different addressable elements. This embodiment of the array can be used to simultaneously detect the expression of the following 10 human genes in a biological sample: NKX2-3, DLX1, HOXC4, HOXC6, PSGR, PCA3, PCGEM1, ERG, COL10A1, and CTBP1.

In another embodiment, the array comprises (a) a substrate and (b) 6 or more different addressable elements that each comprise at least one polynucleotide probe for detecting the expression of an mRNA transcript (or cDNA synthesized from the mRNA transcript) of one of the following human genes: DLX1, NKX2-3, COL10A1, HOXC4, PSGR, and HOXC6, wherein the array comprises no more than 500, no more than 250, no more than 100, no more than 50, no more than 25, no more than 15, or no more than 10 different addressable elements. In certain embodiments, the array contains no more than 100 different addressable elements. In certain embodiments, the array contains no more than 25 different addressable elements. In certain embodiments, the array contains no more than 15 different addressable elements. This embodiment of the array can be used to simultaneously detect the expression of the following 6 human genes in a biological sample: DLX1, NKX2-3, COL10A1, HOXC4, PSGR, and HOXC6.

In another embodiment, the array comprises (a) a substrate and (b) 6 or more different addressable elements that each comprise at least one polynucleotide probe for detecting the expression of an mRNA transcript (or cDNA synthesized from the mRNA transcript) of one of the following human genes: PSGR, DLX1, HOXC4, NKX2-3, PCA3, and ERG, wherein the array comprises no more than 500, no more than 250, no more than 100, no more than 50, no more than 25, no more than 15, or no more than 10 different addressable elements. In certain embodiments, the array contains no more than 100 different addressable elements. In certain embodiments, the array contains no more than 25 different addressable elements. In certain embodiments, the array contains no more than 15 different addressable elements. This embodiment of the array can be used to simultaneously detect the expression of the following 6 human genes in a biological sample: PSGR, DLX1, HOXC4, NKX2-3, PCA3, and ERG.

In another embodiment, the array comprises three or more different addressable elements each of which comprises at least one polynucleotide probe for detecting the expression of an mRNA transcript (or cDNA synthesized from the mRNA transcript) of one of the following human genes: PCA3, PCGEM1, and PSGR, wherein the array comprises no more than 500, no more than 250, no more than 100, no more than 50, no more than 25, no more than 15, no more than 10, or no more than 5 different addressable elements. In certain embodiments, the array contains no more than 100 different addressable elements. In certain embodiments, the array contains no more than 10 different addressable elements. In certain embodiments, the array contains no more than 5 different addressable elements. This embodiment of the array can be used to simultaneously detect the expression of the following 3 human genes in a biological sample: PCA3, PCGEM1, and PSGR.

An array can also be used to measure protein levels of multiple proteins in parallel. Such an array comprises one or more supports bearing a plurality of ligands that specifically bind to a plurality of proteins, wherein the plurality of proteins comprises no more than 500, no more than 250, no more than 100, no more than 50, no more than 25, or no more than 15 different proteins. The ligands are optionally attached to a planar support or beads. In one embodiment, the ligands are antibodies. The proteins that are to be detected using the array correspond to the proteins encoded by the nucleic acids of interest, as described above, including the specific gene expression profiles disclosed. Thus, each ligand (e.g. antibody) is designed to bind to one of the target proteins (e.g., polypeptide sequences encoded by the genes disclosed herein). As with the nucleic acid arrays, each ligand may be associated with a different addressable element to facilitate detection of the different proteins in a sample.

In certain embodiments, disclosed herein are methods of obtaining a gene expression profile in a biological sample, such as a urine sample, the method comprising: a) incubating an array as disclosed herein with the biological sample; and b) measuring the expression level of the genes of interest.

For example, in certain embodiments, disclosed herein are methods of obtaining a gene expression profile in a biological sample obtained from a patient of African descent, the method comprising: a) incubating an array with the biological sample; and b) measuring the expression level of at least the following genes: PCA3, PCGEM1, and PSGR, and optionally an ERG gene, to obtain the gene expression profile. According to certain embodiments, the method of obtaining a gene expression profile comprises a) incubating an array with the biological sample; and b) measuring the expression level of at least the following genes: DLX1, NKX2-3, COL10A1, HOXC4, PSGR, and HOXC6, and optionally an ERG gene, to obtain the gene expression profile. According to certain embodiments, the method of obtaining a gene expression profile comprises a) incubating an array with the biological sample; and b) measuring the expression level of at least the following genes: PSGR, DLX1, HOXC4, NKX2-3, PCA3, and ERG to obtain the gene expression profile. In certain embodiments the method of obtaining a gene expression profile comprises a) incubating an array with the biological sample; and b) measuring the expression level of at least the following genes: NKX2-3, DLX1, HOXC4, HOXC6, PSGR, PCA3, PCGEM1, ERG, COL10A1, and CTBP1 to obtain the gene expression profile. The biological sample may be, for example, a tissue sample, a cell sample, a blood sample, a serum sample, or a urine sample. In certain embodiments of the methods disclosed herein, the biological sample comprises nucleic acids or polypeptides isolated from prostate cells or exosomes derived therefrom.

Urine Exosome Assay

Disclosed herein are assays and assay protocols for use with RNA derived from exosomes, such as urine-derived exosomes. Methods of obtaining gene expression signatures using exosomes in urine samples is disclosed, for example, in US20160177401, which is hereby incorporated by reference in its entirety.

In some embodiments, disclosed herein is a method of obtaining a gene expression profile in a urine sample from a patient, the method comprising detecting mRNA expression of a plurality of genes, wherein the plurality of genes comprises 1) PCA3, PCGEM1, and PSGR; or 2) at least 6 of the following genes: NKX2-3, DLX1, HOXC4, HOXC6, PSGR, PCA3, PCGEM1, ERG, COL10A1, and CTBP1, and wherein the detecting step comprises detecting mRNA that has been obtained from exosomes in the urine sample. In certain embodiments, the mRNA from the exosomes is converted to cDNA and amplified prior to the detecting step. In certain embodiments, the method further comprises isolating exosomes from the urine sample. In certain embodiments, the method further comprises extracting mRNA from the exosomes. In certain embodiments, the method further comprises a step of converting the extracted mRNA to cDNA and amplifying the cDNA (e.g., RT-PCR). In certain embodiments, the method further comprises a step of normalizing the expression of the plurality of genes to a control (e.g., SPDEF). In certain embodiments, the method comprises detecting mRNA expression of at least the following genes: DLX1, NKX2-3, COL10A1, HOXC4, PSGR, and HOXC6. In certain embodiments, the method comprises detecting mRNA expression of at least the following genes: PSGR, DLX1, HOXC4, NKX2-3, PCA3, and ERG. In certain embodiments, the method comprises detecting mRNA expression of at least the following genes: NKX2-3, DLX1, HOXC4, HOXC6, PSGR, PCA3, PCGEM1, ERG, COL10A1, and CTBP1.

In certain embodiments, the gene expression profile obtained from the exosomes in the urine sample is used to diagnose or prognose prostate cancer, wherein overexpression of at least one of the following genes: NKX2-3, DLX1, HOXC4, HOXC6, PSGR, PCA3, PCGEM1, ERG, COL10A1, and CTBP1 as compared to a control or a threshold value indicates the presence of prostate cancer in the biological sample. In certain embodiments, overexpression of at least one of the following genes: DLX1, NKX2-3, COL10A1, HOXC4, PSGR, and HOXC6 as compared to a control or a threshold value indicates the presence of prostate cancer in the biological sample. In certain embodiments, overexpression of at least one of the following genes: PSGR, DLX1, HOXC4, NKX2-3, PCA3, and ERG as compared to a control or a threshold value indicates the presence of prostate cancer in the biological sample.

In certain embodiments, the gene expression in the exosome assay is normalized by a control gene, such as SPDEF. In certain embodiments, the urine sample is a digital rectal exam (DRE) urine sample. In other embodiments, the urine sample is a non-DRE urine sample that is collected without using a DRE or prostatic massage prior to urine collection. In certain embodiments, the urine sample is the urine that is first voided from the bladder, also known as "first catch" urine. The first voided urine contains the highest concentration of prostate-derived microvesicles, and therefore the analysis of the first voided urine provides higher signal from prostate biomarkers. In certain embodiments, the urine sample is the first 40 mL or less, voided from the bladder. For example, the urine sample is the first 20 mL voided from the bladder.

In certain embodiments, a subject who provided the urine sample is diagnosed with prostate cancer when at least one of the genes in the assay is overexpressed. Overexpression of the at least one gene may, in certain embodiments, be overexpression that is at least about 1.2-fold, 1.5-fold, 2-fold, 2.5-fold, 4-fold, 5-fold, 10-fold, 20-fold, 50-fold, 100-fold higher or even greater expression as compared to a control gene (e.g., SPDEF) or threshold value.

In certain embodiments, the sensitivity of the exosome assay, or the ability of the assay to correctly identify a subject with prostate cancer, is at least about 65%, at least about 70%, at least about 75%, at least about 80%, or at least about 85%. In certain embodiments, the specificity of the exosome assay, or the ability of the assay to correctly identify a subject without prostate cancer, is at least about 60%, such as at least about 65%, at least about 70%, or at least about 75%.

Patient Treatment

Disclosed herein are methods of diagnosing prostate cancer in a sample obtained from a subject, in which gene expression in prostate cells and/or tissues is analyzed. If a sample shows over-expression of certain genes, then there is an increased likelihood that the subject has prostate cancer. In the event of such a result, the methods of detecting prostate cancer may include one or more of the following steps: informing the patient that they are likely to have prostate cancer; confirmatory histological examination of prostate tissue; and/or treating the patient by a prostate cancer therapy.

Thus, in certain aspects, if the detection step indicates that the subject has prostate cancer, the methods further comprise a step of taking a prostate biopsy from the subject and examining the prostate tissue in the biopsy (e.g., histological examination) to confirm whether the patient has prostate cancer. Alternatively, the methods of detecting or prognosing prostate cancer may be used to assess the need for therapy or to monitor a response to a therapy (e.g., disease-free recurrence following surgery or other therapy), and, thus may include an additional step of treating a subject having prostate cancer.

Prostate cancer treatment options include surgery, radiation therapy, hormone therapy, chemotherapy, biological therapy, or high intensity focused ultrasound. Drugs approved for prostate cancer include: Enzalutamide (XTANDI), Abiraterone Acetate, Cabazitaxel, Degarelix, Jevtana (Cabazitaxel), Prednisone, Provenge (Sipuleucel-T), or Docetaxel. Thus a method as described herein may, after a positive result, include a further treatment step, such as, surgery, radiation therapy, hormone therapy, chemotherapy, biological therapy, or high intensity focused ultrasound.

Disclosed herein are methods of identifying a patient in need of prostate cancer treatment, the method comprising testing a biological sample from the patient for the overexpression of a plurality of genes; and identifying the patient as in need of prostate cancer treatment if one or more of the genes is overexpressed in the biological sample as compared to a control. In certain embodiments, the patient is of African descent, the plurality of genes is selected because the patient is of African descent, and the plurality of genes comprises at least the following genes: PCA3, PCGEM1, and PSGR.

Also disclosed herein are methods of identifying a patient in need of prostate cancer treatment, the method comprising a) testing a biological sample from the patient for the overexpression of a plurality of genes, wherein the plurality of genes comprises at least the following genes: DLX1, NKX2-3, COL10A1, HOXC4, PSGR, and HOXC6; and b) identifying the patient as in need of prostate cancer treatment if one or more of the DLX1, NKX2-3, COL10A1, HOXC4, PSGR, and HOXC6 genes is overexpressed in the biological sample as compared to a control.

In further embodiments disclosed herein, there are methods of identifying a patient in need of prostate cancer treatment, the method comprising a) testing a biological sample from the patient for the overexpression of a plurality of genes, wherein the plurality of genes comprises at least the following genes: PSGR, DLX1, HOXC4, NKX2-3, PCA3, and ERG; and b) identifying the patient as in need of prostate cancer treatment if one or more of the PSGR, DLX1, HOXC4, NKX2-3, PCA3, and ERG genes is overexpressed in the biological sample as compared to a control.

Also disclosed herein are methods of identifying a patient in need of prostate cancer treatment, the method comprising a) testing a biological sample from the patient for the overexpression of a plurality of genes, wherein the plurality of genes comprises at least the following genes: NKX2-3, DLX1, HOXC4, HOXC6, PSGR, PCA3, PCGEM1, ERG, COL10A1, and CTBP1; and b) identifying the patient as in need of prostate cancer treatment if one or more of the NKX2-3, DLX1, HOXC4, HOXC6, PSGR, PCA3, PCGEM1, ERG, COL10A1, and CTBP1 genes is overexpressed in the biological sample as compared to a control.

In certain embodiments, the methods of identifying a patient in need of prostate cancer treatment further comprise a step of treating the patient identified as in need of prostate cancer, and in certain embodiments, the sample is a urine sample that comprises exosomes.

Disclosed herein are methods of treating prostate cancer in a patient, comprising a) testing a biological sample, such as a urine sample that comprises exosomes, from the patient for the expression of a plurality of genes, wherein the plurality of genes comprises at least six of the following genes: NKX2-3, DLX1, HOXC4, HOXC6, PSGR, PCA3, PCGEM1, ERG, COL10A1, and CTBP1; and treating the patient if the testing in step a) reveals that the patient overexpresses as compared to a control one or more of the following genes: NKX2-3, DLX1, HOXC4, HOXC6, PSGR, PCA3, PCGEM1, ERG, COL10A1, and CTBP1. In certain embodiments, the plurality of genes comprises at least the following six genes: DLX1, NKX2-3, COL10A1, HOXC4, PSGR, and HOXC6. In certain other embodiments, the plurality of genes comprises at least the following six genes: PSGR, DLX1, HOXC4, NKX2-3, PCA3, and ERG. In other embodiments, the plurality of genes comprises at least the following genes: NKX2-3, DLX1, HOXC4, HOXC6, PSGR, PCA3, PCGEM1, ERG, COL10A1, and CTBP1.

In other embodiments, the method comprises a) testing a biological sample, such as a urine sample that comprises exosomes, from a patient for the expression of a plurality of genes, wherein the plurality of genes comprises the following genes: PCA3, PCGEM1, and PSGR; and treating the patient if the testing in step a) reveals that the patient overexpresses as compared to a control one or more of the following genes: PCA3, PCGEM1, and PSGR, wherein the patient is of African descent, and the plurality of genes is selected because the patient is of African descent.

Drug Screening

The gene expression profiles associated with prostate cancer or lack thereof provided by the methods described herein can also be useful in screening drugs, either in clinical trials or in animal models of prostate cancer. A clinical trial can be performed on a drug in similar fashion to the monitoring of an individual patient, except that the drug is administered in parallel to a population of prostate cancer patients, usually in comparison with a control population administered a placebo.

The changes in expression levels of genes can be analyzed in individual patients and across a treated or control population. Analysis at the level of an individual patient provides an indication of the overall status of the patient at the end of the trial (i.e., whether gene expression profile indicates the presence or severity (e.g., well-differentiated (WD) prostate cancer or poorly differentiated (PD) prostate cancer) of prostate cancer) and/or an indication whether that profile has changed toward or away from such indication in the course of the trial. Results for individual patients can be aggregated for a population allowing comparison between treated and control population.

Similar trials can be performed in non-human animal models of prostate cancer. In this case, the expression levels of genes detected are the species variants or homologs of the human genes referenced above in whatever species of non-human animal on which tests are being conducted. Although the average expression levels of human genes determined in human prostate cancer patients are not necessarily directly comparable to those of homolog genes in an animal model, the human values can nevertheless be used to provide an indication whether a change in expression level of a non-human homolog is in a direction toward or away from the diagnosis of prostate cancer or prognosis of WD or PD prostate cancer. The expression profile of individual animals in a trial can provide an indication of the status of the animal at the end of the trial (i.e., whether gene expression profile indicates the presence or severity (e.g., WD or PD) of prostate cancer) and/or change in such status during the trial. Results from individual animals can be aggregated across a population and treated and control populations compared. Average changes in the expression levels of genes can then be compared between the two populations.

Kits

The polynucleotide probes and/or primers or antibodies or polypeptide probes that can be used in the methods described herein can be arranged in a kit. Thus, one embodiment is directed to a kit for diagnosing or prognosing prostate cancer comprising a plurality of polynucleotide probes for detecting at least 6 of the following human genes: NKX2-3, DLX1, HOXC4, HOXC6, PSGR, PCA3 (aka DD3), PCGEM1, ERG, COL10A1, and CTBP1, wherein the plurality of polynucleotide probes contains polynucleotide probes for no more than 500, 250, 100, 50, 25, 15, or 10 genes. In one embodiment, the plurality of polynucleotide probes comprises polynucleotide probes for detecting all 10 of the aforementioned genes, wherein the plurality of polynucleotide probes contains polynucleotide probes for no more than 15 genes. In one embodiment, the plurality of polynucleotide probes comprises polynucleotide probes for detecting at least 6 or 8 of the aforementioned genes, wherein the plurality of polynucleotide probes contains polynucleotide probes for no more than 10 genes. In one embodiment, the plurality of polynucleotide probes comprises polynucleotide probes for detecting the following 6 genes: DLX1, NKX2-3, COL10A1, HOXC4, PSGR, and HOXC6. In another embodiment, the plurality of polynucleotide probes comprises polynucleotide probes for detecting the following 6 genes: PSGR, DLX1, HOXC4, NKX2-3, PCA3, and ERG. In one embodiment, the kit comprises at least one oligonucleotide probe for detecting the expression of a control gene, such as, one of the following human genes: PSA and SPDEF. The polynucleotide probes may be optionally labeled.

The kit may optionally include polynucleotide primers for amplifying a portion of the mRNA transcripts from at least 6 of the following human genes: NKX2-3, DLX1, HOXC4, HOXC6, PSGR, PCA3 (aka DD3), PCGEM1, ERG, COL10A1, and CTBP1. In one embodiment, the kit optionally includes polynucleotide primers for amplifying a portion of the mRNA transcripts from all 10 of the aforementioned genes. In one embodiment, the kit optionally includes polynucleotide primers for amplifying a portion of the mRNA transcripts from the following 6 genes: DLX1, NKX2-3, COL10A1, HOXC4, PSGR, and HOXC6. In one embodiment, the kit optionally includes polynucleotide primers for amplifying a portion of the mRNA transcripts from the following 6 genes: PSGR, DLX1, HOXC4, NKX2-3, PCA3, and ERG. In one embodiment, the kit comprises polynucleotide primers for amplifying a portion of the mRNA transcripts from a control gene, such as, one of the following human genes: PSA and SPDEF.

Another embodiment is directed to a kit for diagnosing or prognosing prostate cancer in a patient of African descent, the kit comprising a plurality of polynucleotide probes for detecting the following human genes: PCA3, PCGEM1, and PSGR, wherein the plurality of polynucleotide probes contains polynucleotide probes for no more than 500, 250, 100, 50, 25, 15, or 10 genes. Preferably, the kit contains polynucleotide probes for no more than 10, 9, 8, 7, 6, or 5 genes. In one embodiment, the kit comprises at least one oligonucleotide probe for detecting the expression of a control gene, such as, one of the following human genes: PSA and SPDEF. The polynucleotide probes may be optionally labeled.

The kit may optionally include polynucleotide primers for amplifying a portion of the mRNA transcripts from the following human genes: PCA3, PCGEM1, and PSGR. In one embodiment, the kit comprises polynucleotide primers for amplifying a portion of the mRNA transcripts from a control gene, such as, one of the following human genes: PSA and SPDEF.

The kit for diagnosing or prognosing prostate cancer may also comprise antibodies. Thus, in one embodiment, the kit for diagnosing or prognosing prostate cancer comprises a plurality of antibodies for detecting at least 6 of the polypeptides encoded by the following human genes: NKX2-3, DLX1, HOXC4, HOXC6, PSGR, PCA3 (aka DD3), PCGEM1, ERG, COL10A1, and CTBP1, wherein the plurality of antibodies contains antibodies for no more than 500, 250, 100, 50, 25, 15, or 10 polypeptides. In one embodiment, the plurality of antibodies comprises antibodies for detecting at least 6 or 8 of the polypeptides encoded by the aforementioned genes and wherein the plurality of antibodies contains antibodies for no more than 12 polypeptides. In one embodiment, the plurality of antibodies comprises antibodies for detecting the polypeptides encoded by the following 6 genes: DLX1, NKX2-3, COL10A1, HOXC4, PSGR, and HOXC6, and in one embodiments, the plurality of antibodies comprises antibodies for detecting the polypeptides encoded by the following 6 genes: PSGR, DLX1, HOXC4, NKX2-3, PCA3, and ERG. In one embodiment, the plurality of antibodies comprises antibodies for detecting the polypeptides encoded by the 10 aforementioned genes. The antibodies may be optionally labeled.

In another embodiment, the kit for diagnosing or prognosing prostate cancer in a patient of African descent comprises a plurality of antibodies for detecting at least the following human genes: PCA3, PCGEM1, and PSGR, wherein the plurality of antibodies contains antibodies for no more than 500, 250, 100, 50, 25, 15, 10, or 5 polypeptides. The antibodies may be optionally labeled.

As noted above, the polynucleotide or polypeptide probes and antibodies described herein may be optionally labeled with a detectable label. Any detectable label used in conjunction with probe or antibody technology, as known by one of ordinary skill in the art, can be used. In certain embodiments, the probe or antibody is labeled with a detectable label selected from the group consisting of a fluorescent label, a chemiluminescent label, a quencher, a radioactive label, biotin, mass tags and/or gold.

In one embodiment, a kit includes instructional materials disclosing methods of use of the kit contents in a disclosed method. The instructional materials may be provided in any number of forms, including, but not limited to, written form (e.g., hardcopy paper, etc.), in an electronic form (e.g., computer diskette or compact disk) or may be visual (e.g., video files). The kits may also include additional components to facilitate the particular application for which the kit is designed. Thus, for example, the kits may additionally include other reagents routinely used for the practice of a particular method, including, but not limited to buffers, enzymes, labeling compounds, and the like. Such kits and appropriate contents are well known to those of skill in the art. The kit can also include a reference or control sample. The reference or control sample can be a biological sample or a data base.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Three platforms (RNASeq, NanoString and q-RT-PCR) were used for evaluation of CaP associated gene expression in CA and AA patients (N=144). Candidate genes with robust tumor over-expression (over 4-fold) in CaP in comparison to paired normal and tumor specimens from AA and CA patients were selected from the NanoString and RNASeq data for validation by qRT-PCR (TaqMan®) in laser microdissected (LCM) tumor and benign cells of frozen tissue sections (50 CA and 35 AA). An assay protocol (gene specific pooled RT and pre-amplification followed by TaqMan® PCR) was set up for the noninvasive early detection of candidate genes in regular patient urine (non-DRE) using RNA derived from urinary exosomes.

Prostate Cancer Specimens

Prostate cancer samples selected for the present study included archived specimens, which included formalin-fixed paraffin-embedded (FFPE) and frozen optimal cutting temperature (OCT) embedded samples, obtained under an IRB approved protocol from patients undergoing radical prostatectomy treatment at Walter Reed National Military Medical Center. Non-DRE urine samples were collected after informed consent from men (screening/before biopsy) undergoing diagnostic biopsy.

Urine Collection and Preparation

Urine samples were collected in urine collection cups containing DNA/RNA preservative (Sierra Diagnostics LLC). The urine sample was mixed 11:1 with the buffer. Urine samples were spun at 1000 rpm for 10 min to remove the exfoliated urinary cells. Supernatant was aliquoted and frozen at −80° C. To guarantee optimal sample quality all samples were processed within 48 hours after collection.

Isolation of Total RNA from Exosomes in Urine

Exosome mRNA extraction from fresh frozen urine (5 ml) was done using Urine Exosome RNA Isolation Kit (Norgen Biotek Corp.; Cat. 47200).

RNA Sequencing

Total RNA from 18 (AA=9; CA=9, including 4 normal) histological defined and manually micro-dissected OCT-embedded frozen tissue sections was extracted using an RNA extraction kit. RNA integrity was assessed using the Agilent RNA 6000 Pico Kit on the Agilent 2100 BioAnalyzer (Agilent Technologies Inc. Columbia, MD). Resultant RNA was used for library preparation using the TruSeq® RNA Library Prep Kit v2 (Illumina, San Diego, CA). Sequencing libraries were prepared, and libraries were assessed for size distribution using the Experion DNA HighSens Analysis Kit and quantified by qPCR using the Kapa Library Quantification Kit for Illumina (KAPA Biosystems, Wilmington, MA). Libraries were sequenced on a Genome Analyzer IIx (Illumina) with paired-end 75 bp reads for at least 35 million reads per sample. FASTQ data was quality controlled by using FastQC before expression abundance count analysis, performed using the Tuxedo Suite of TopHat, Bowtie and Cufflinks on Galaxy.

nCounter® Analysis

NanoString profiling in archived, whole-mounted FFPE prostate specimens was performed on 151-CaP probe set. The values were based on NanoString readouts for tumor vs. normal fold change (>4) and p-value (<0.01) (Norgen Biotek Corp.; Cat. 47200).

qRT-PCR

Gene specific cDNA synthesis. All the genes were reverse transcribed in a single reaction using Omniscript RT Kit (Qiagen) using a gene specific primer (GSP) pool of custom designed reverse primers. GSP pool (final concentration 10 μM) was prepared using reverse primers for the candidate genes. Reaction mixture included RNA (100 pg for tissue based and 5 ng for urine exosome based analysis), GSP pool (1 μM final), 1×RT buffer, dNTPs (0.5 mM each), RNase Inhibitor (10 units), and Omniscript RT enzyme (4 units). Reverse transcription reaction was performed at +37° C. for 60 min followed by +93° C. for 5 min, and then held at +10° C. GAPDH and SPDEF were included as normalizing controls for tissue and urine based mRNA expression analysis, respectively.

Taqman® Pre-amplification. The gene specific cDNA (100 pg final concentration) was preamplified using TaqMan® Pre-Amp Master Mix (Life Technologies) and forward and reverse primers (55 nM final concentration) for the target genes. The protocol was adapted and modified from Knezevic et al., *Analytical validation of the Oncotype DX prostate cancer assay—a clinical RT-PCR assay optimized for prostate needle biopsies*, BMC GENOMICS, 14:690, 2013. The reactions conditions included enzyme activation of 95° C. for 10 min followed by 8 preamplification cycles at 95° C. for 15 sec and 60° C. for 4 min.

qPCR. The preamplification product was diluted 1:5 with water. qPCR was performed on the diluted amplified product with TaqMan® gene expression master mix (Life Technologies), optimized forward and reverse primers, and probes for each of the expression assays on Mx3000P qPCR System (Agilent Technologies). The PCR conditions included 55° C. for 2 min followed by initial denaturation at 95° C. for 10 min and 50 cycles at 95° C. for 30 sec, 56° C. for 1 min, and 72° C. for 1 min.

Statistical Analysis. Expression was measured in cycle threshold (Ct) values in log 2 values. Expression was normalized to GAPDH for tissue based analysis and SPDEF for urine exosome based analysis. The mRNA expression data was analyzed according to relative quantification method, as ΔCt=Ct GAPDH−Ct target. Fold difference between any two samples was calculated as fold=2^(ΔCt1−ΔCt2).

Biomarker Candidate Selection

Nine genes, including PCA3, AMACR, and ERG, were selected from the transcriptome analysis of tumors by the RNA-Seq and Nanostring approaches discussed above. FIGS. 2A-D are heatmaps displaying mRNA expression levels assessed by qRT-PCR for the 9 selected genes (DLX1, NKX2-3, HOXC4, COL10A1, PSGR, HOXC6 PCA3, AMACR and ERG3) in laser capture micro-dissected matched tumor-normal prostate tissue of 35 AA and 50 CA patients. Column numbers represent individual patients (N=85). Rows represent genes of the panel, wherein shaded squares represent T/N ratio≥4-fold; white squares represent T/N ratio<4-fold; and striped squares represent positive cumulative expression of the gene panel by patients. Based on a 4-fold overexpression cutoff in tumor cells in 35 AA and 50 CA patients, it can be calculated from FIG. 2A that the performance of the 3-panel expression levels for the 35 AA patients was 71.5% positive (25 out of 35 patients). The performance of the 3-panel expression levels for the 50 CA patients was 92% positive (46 out of 50 patients). See FIG. 2B. To address this discrepancy between the CA and AA patients and to improve the current biomarker panel, qPCR data based on CaP tissue identified a 6-gene marker panel. At least one gene of a six-gene signature (PSGR, DLX1, NKX2-3, HOXC6, HOXC4 and PCA3) was over-expressed in tumor cells of all AA and CA cases (85 of 85 patients), providing a consistent ethnicity informed tumor expression signature. See FIGS. 2C and 2D.

Biomarker candidate selection was validated by The Cancer Genome Atlantis (TCGA) RNASeq data on 40 tumor-normal matched CaP patients. Strong concordance was found for TCGA and Center for Prostate Disease Research (CPDR) datasets based on >4 fold T/N expression and copy number of candidate markers, as shown below in Table 1 and in FIGS. 3A-B. Table 1 provides normalised RNA seq counts in tumor tissue for the 9 genes in the TCGA and CPDR RNASeq datasets.

TABLE 1

| | TCGA_RNA Seq Counts | CPDR_RNA Seq Counts |
|---|---|---|
| PCA3 | 8205 | 10916 |
| ERG | 2858 | 4128 |
| AMACR | 12988 | 3385 |
| PSGR | 13185 | 16292 |
| DLX1 | 537 | 626 |
| HOXC6 | 293 | 133 |
| COL10A1 | 172 | 868 |
| HOXC4 | 110 | 44 |
| NKX2-3 | 32 | 60 |

Figure 3A:
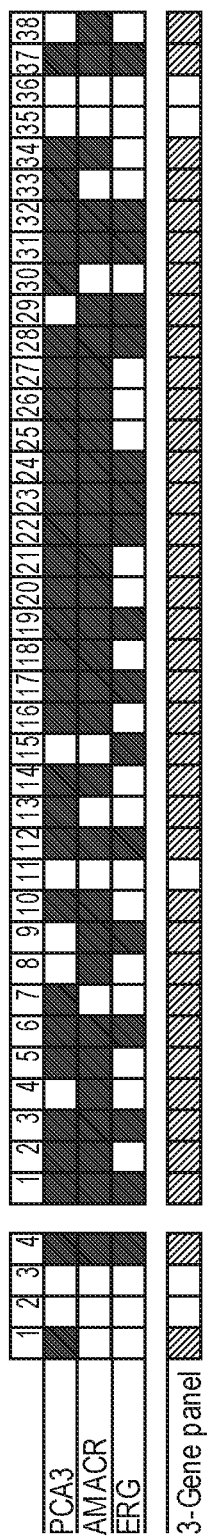
FIG. 3A is a heatmap displaying mRNA expression levels assessed by RNA-Seq for three selected genes (PCA, AMACR, and ERG3) in matched, tumor-normal prostate tissue of 4 AA (left panels) and 38 CA (right panels) patients.
Figure 3B:
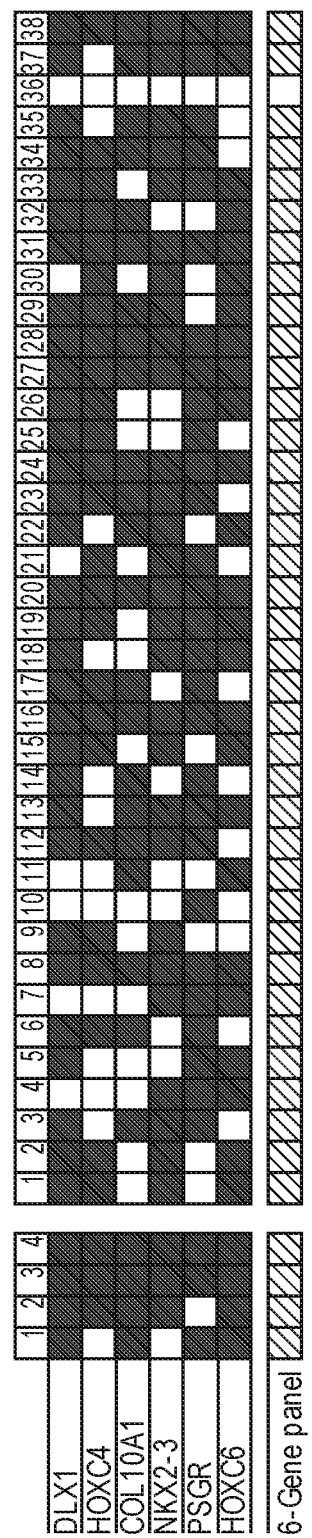
FIG. 3B is a heatmap displaying mRNA expression levels assessed by RNA-Seq for six selected genes (DLX1, HOXC4, COL10A1, NKX2-3, PSGR, and HOXC6) in matched, tumor-normal prostate tissue of 4 AA (left panels) and 38 CA (right panels) patients.

FIGS. 3A and 3B are heatmaps displaying mRNA expression levels assessed by RNA-Seq for the 9 selected genes (DLX1, NKX2-3, HOXC4, COL10A1, PSGR and HOXC6 shown in FIG. 3B; PCA3, AMACR and ERGS shown in FIG. 3A) in matched tumor-normal prostate tissue of 4 AA (left columns 1-4) and 38 CA patients (right columns 1-38). Column numbers represent individual patients (N=42), and rows represent genes of the panel. Shaded boxes represent T/N ratio≥4-fold; white boxes represent T/N ratio<4-fold;

and striped boxes represent a positive cumulative expression of the gene panel by the patient.

Urinary Exosome Based Assay

These candidate genes and additional markers (PCA3, ERG, PSGR, DLX1, HOXC4, NKX2-3, HOXC6, COL10A1, PCGEM1, CTBP1, with PSA and SPDEF as prostate specific controls) were evaluated in urinary exosome based CaP diagnostic assay platform in patient urine derived exosome specimens. A urinary exosome based assay was developed and optimized for PSGR, DLX1, HOXC4, NKX2-3, as well as PCA3 and ERG. Sensitivity and specificity with optimal cutoff for the urine marker panel was 78.3% and 65.0% respectively (N=40). The assay was further optimized for PSGR, DLX1, HOXC4, NKX2-3, HOXC6, COL10A1, PCGEM1, CTBP1 as well as PCA3 and ERG in regular (non-DRE) urine specimen. The mRNA expression was normalized to the prostate marker SPDEF and an optimal cut-off was determined for each assay.

Figure 4A:
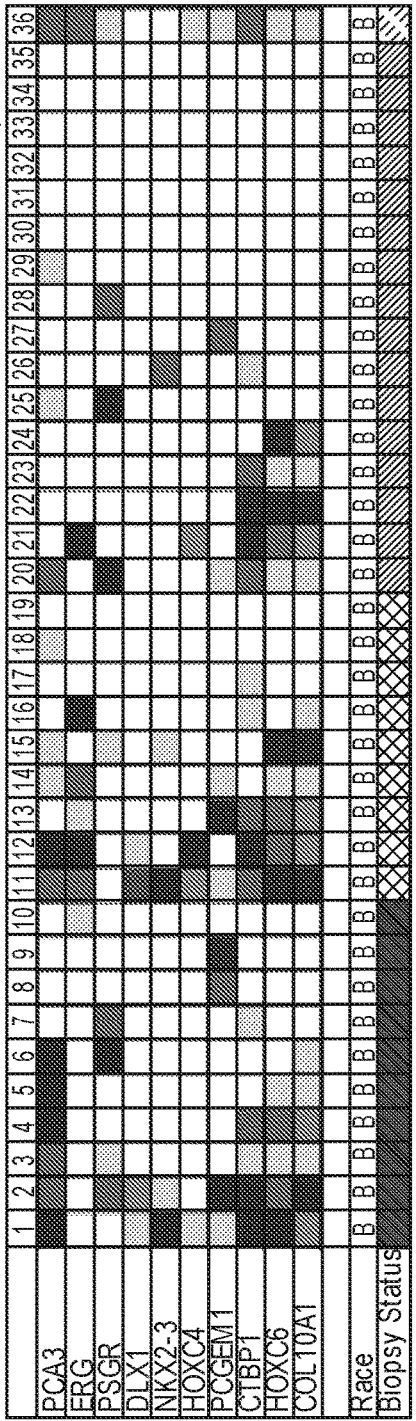
FIG. 4A is a heatmap displaying sensitivity and specificity of mRNA expression for 10 selected genes (PCA3, ERG, PSGR, DLX1, NKX2-3, HOXC4, PCGEM1, CTB1, HOXC6, and COL10A1) in 36 urinary exosome-based AA patient specimens. The solid shaded squares represent gene expression levels, wherein higher expression is indicated by darker shades. The biopsy status for each specimen is also shown as either Gleason Score ("GS")>/=7, GS 3+3, negative, or unknown.
Figure 4B:
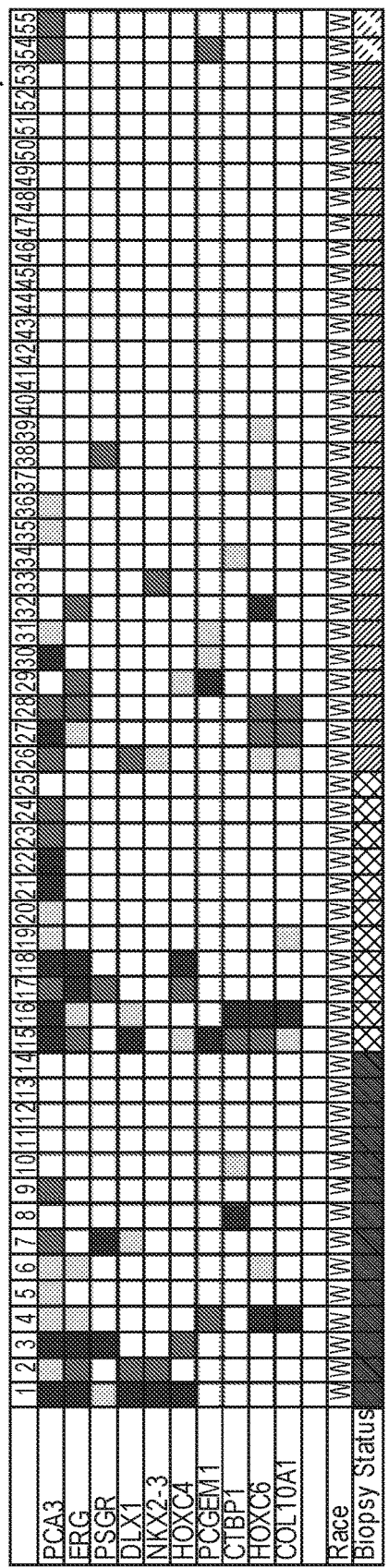
FIG. 4B is a heatmap displaying sensitivity and specificity of mRNA expression for 10 selected genes (PCA3, ERG, PSGR, DLX1, NKX2-3, HOXC4, PCGEM1, CTB1, HOXC6, and COL10A1) in 55 urinary exosome-based CA patient specimens. The solid shaded squares represent gene expression levels, wherein higher expression is indicated by darker shades. The biopsy status for each specimen is also shown as either Gleason Score ("GS")>/=7, GS 3+3, negative, or unknown.

Initial analyses of gene panel for correlation with biopsy positive vs. negative status and low grade vs. high grade prostate cancers in AA and CA patients (N=91) is shown in FIGS. 4A-B. FIGS. 4A-B are heatmaps displaying sensitivity and specificity of 10-marker mRNA expression assay panels in 91 urinary exosome based patient specimens. Column numbers represent individual patients (N=36 AA in FIG. 4A; N=55 CA in FIG. 4B). Rows represent genes of the panel, patent race, and whether the biopsy was positive with a Gleason score≥7, positive with a Gleason score of 6 (3+3); negative, or unknown biopsy status. The solid shaded squares in FIGS. 4A-B represent gene expression levels, wherein higher expression is indicated by darker shades.

Preliminary analysis showed that the 10 marker assay was evaluable in the urine derived exosome RNA specimens. The mRNA expression was normalized to the prostate marker, SPDEF, and an optimal cut-off was determined for each assay. Sensitivity and specificity in non-DRE urine specimens for AA patients with optimal cutoff for the urine marker panel was 94.74% and 37.5% (18 of 19 and 6 of 16, respectively). See FIG. 4A. Sensitivity and specificity in non-DRE urine specimens for CA patients with optimal cutoff for the urine marker panel was 80.0% and 50.0% in CA (20 of 25 and 14 of 28, respectively). See FIG. 4B. Sensitivity and specificity in the CA cohort increased to 84.0% and 51.85% after incorporation of repeat biopsy status. Patients with repeat biopsy were also found to be upgraded to a higher Gleason grade (Gleason Score 7).

Figure 5:
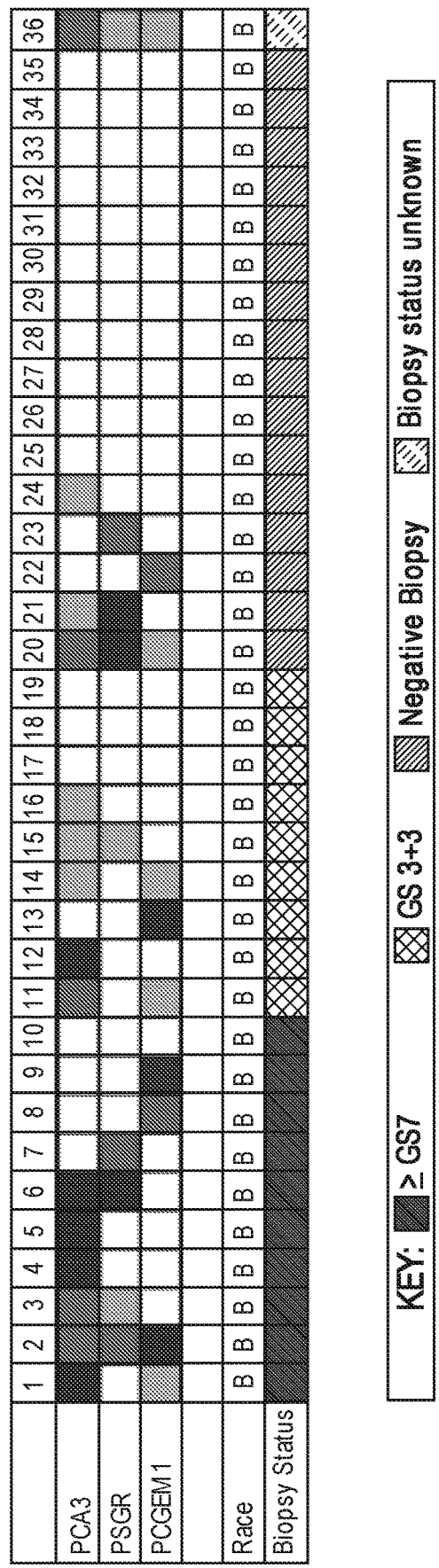
FIG. 5 is a heatmap displaying sensitivity and specificity of mRNA expression of three selected genes (PCA3, PSGR, and PCGEM1) in 36 urinary exosome-based AA patient specimens. The solid shaded squares represent gene expression levels, wherein higher expression is indicated by darker shades. The biopsy status for each specimen is also shown as either Gleason Score ("GS")>/=7, GS 3+3, negative, or unknown.

FIG. 5 is a heatmap displaying sensitivity and specificity of a minimum 3-marker mRNA expression assay panel in 36 urinary exosome-based AA patient specimens. Column numbers represent individual patients (N=36). Rows represent genes of the panel, race, and biopsy status. The solid shaded squares in FIG. 5 represent gene expression levels, wherein higher expression is indicated by darker shades. As shown in FIG. 5, interim analysis for the evaluations of urine exosome gene expression panel in AA CaP patients showed that a minimum 3-gene panel (PCA3, PCGEM1, PSGR) with optimal cut-off has a sensitivity and specificity of 78.9% (15 of 19) and 68.7% (11 of 16), respectively. The urine exosome panel was scored positive in 9 of 10 patients with a biopsy Gleason score of 7 or higher and in 6 of 9 patients with biopsy Gleason score of 6 (3+3). See FIG. 5.

Figure 6:
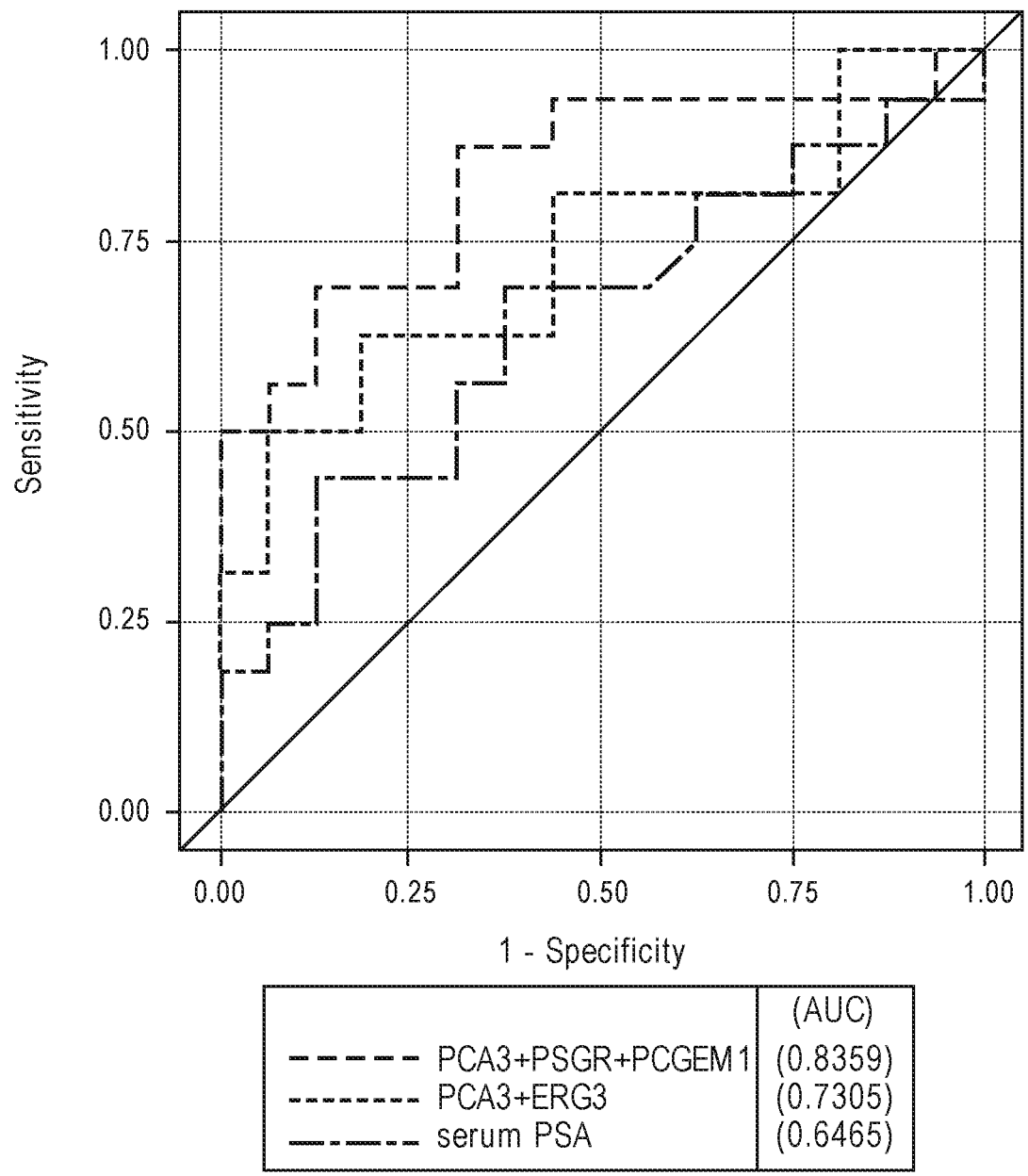
FIG. 6 is a graph comparing the CaP detection sensitivity and specificity of (1) PCA3, PSGR, and PCGEM1; (2) PCA3 and ERG3; and serum PSA in 36 urinary exosome-based AA patient specimens, as measured by the area under the curve (AUC).

The predictive accuracy (AUC) in the 36 AA urine derived exosomal specimens with the 3-gene panel was 0.83. This may be compared to an AUC of 0.64 for PSA and an AUC of 0.73 for the standard PCA3/ERG panel, as shown in FIG. 6.

Figure 7A:
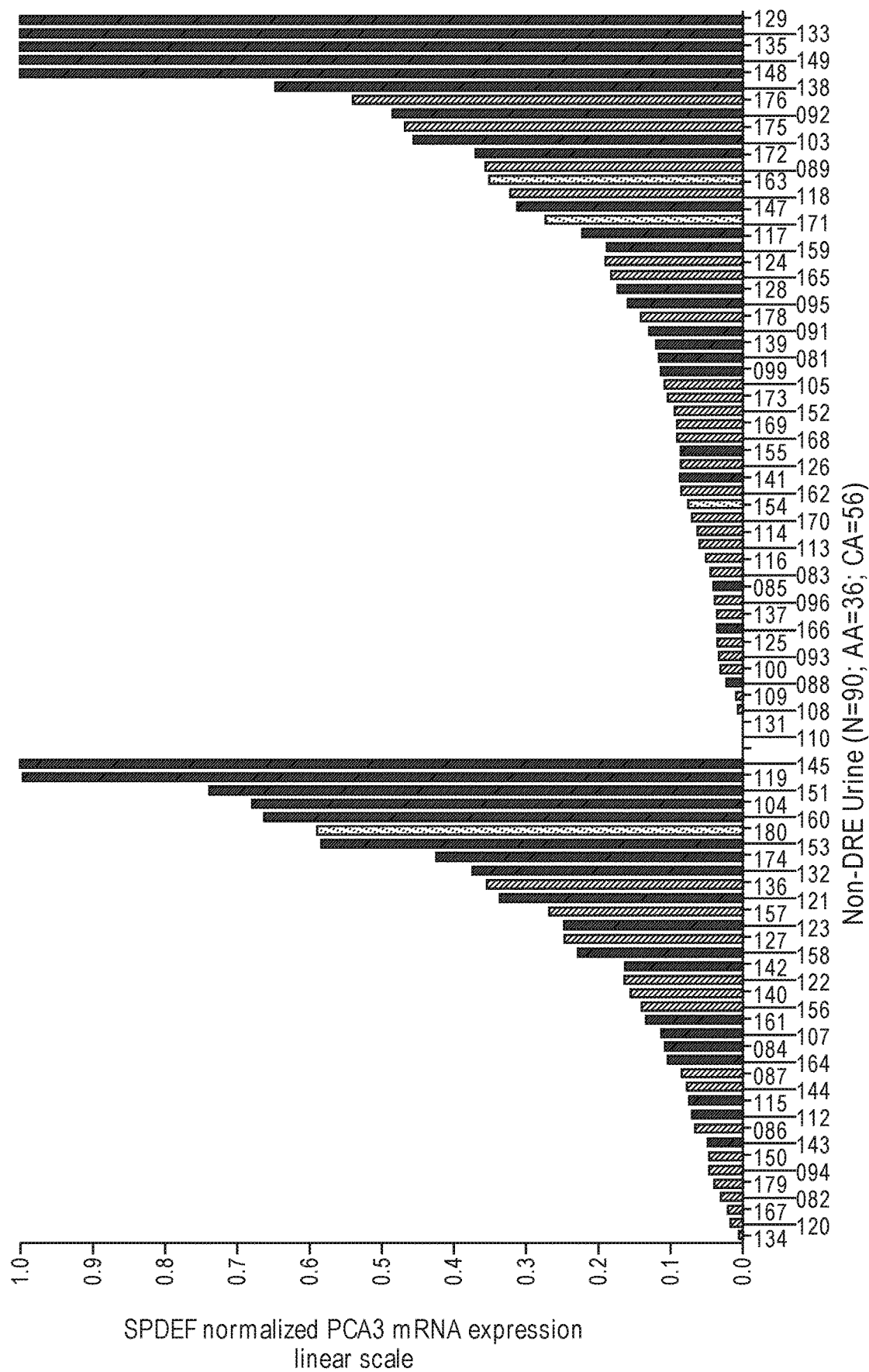
FIG. 7A is a bar graph showing SPDEF-normalized mRNA expression for PCA3 in 91 non-DRE urinary exosome-based patient specimens, where solid shaded bars indicate a positive biopsy, striped bars indicate a negative biopsy, and dotted bars indicate unknown biopsy status.
Figure 7C:
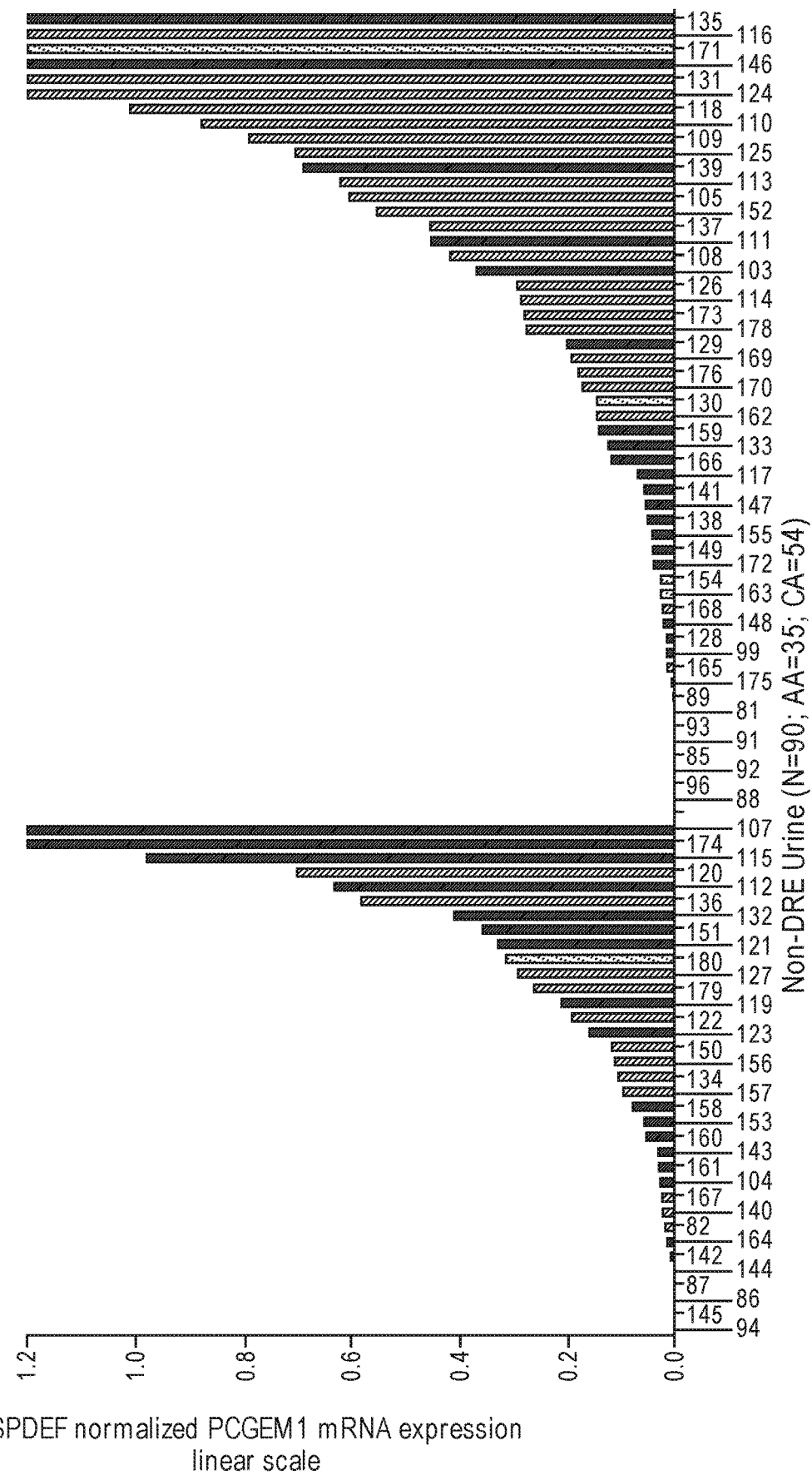
FIG. 7C is a bar graph showing SPDEF-normalized mRNA expression for PCGEM1 in 91 non-DRE urinary exosome-based patient specimens, where solid shaded bars indicate a positive biopsy, striped bars indicate a negative biopsy, and dotted bars indicate unknown biopsy status.

FIGS. 7A-C are bar graphs showing the normalized mRNA readout for PCA3 (FIG. 7A), ERG (FIG. 7B), PCGEM1 (FIG. 7C) in the urinary exosome based patient specimens. Each bar indicates individual patients, wherein solid shaded bars indicate a positive biopsy, striped bars indicate a negative biopsy, and dotted bars indicate unknown biopsy status. AA patient specimens are shown on the left, and CA patient specimens are shown on the right.

Figure 8B:
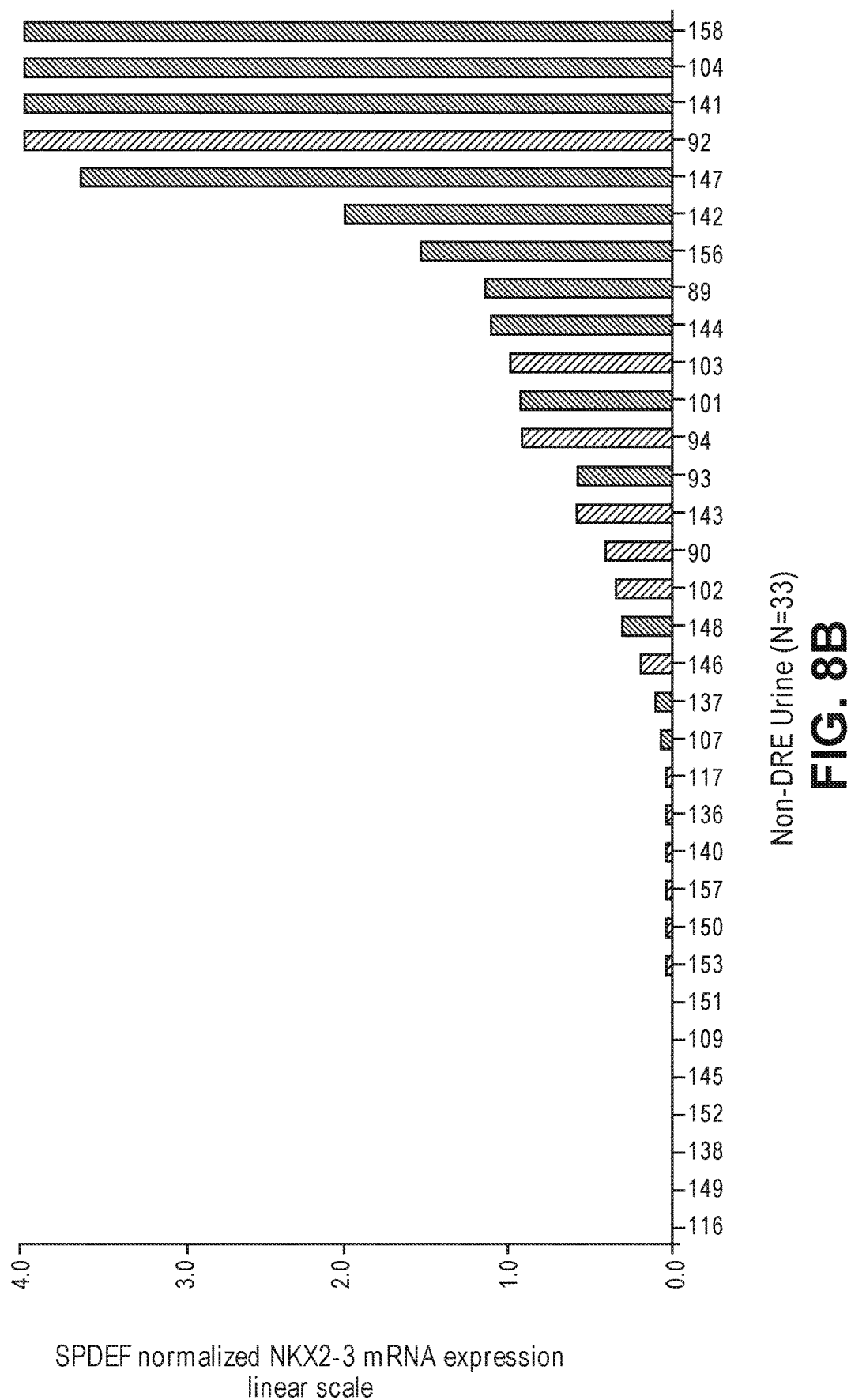
FIG. 8B is a bar graph showing SPDEF-normalized mRNA expression for NKX2-3 in 33 non-DRE urinary exosome-based patient specimens, where narrow stripes indicate a positive biopsy and broad stripes indicate a negative biopsy.
Figure 8E:
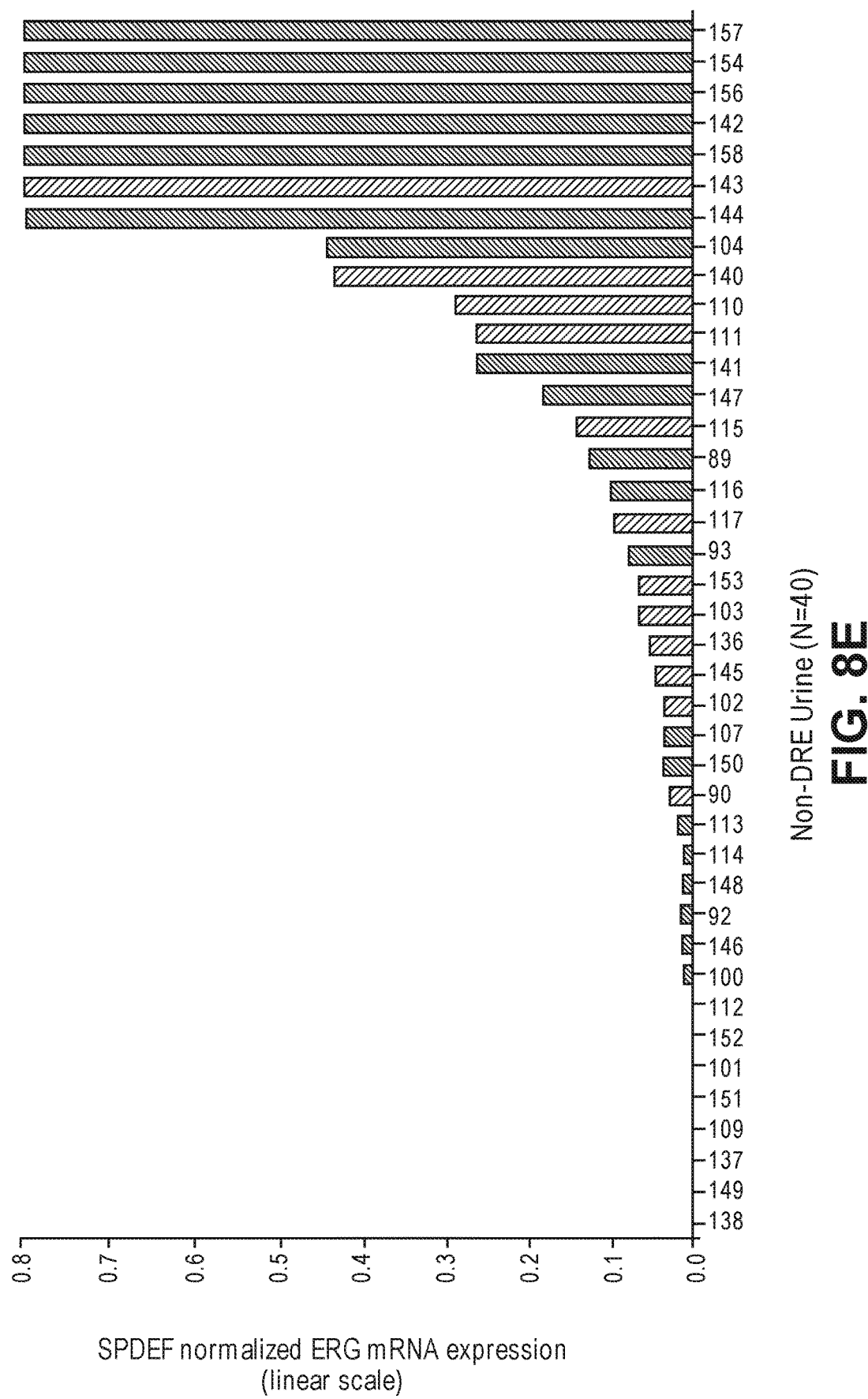
FIG. 8E is a bar graph showing SPDEF-normalized mRNA expression for ERG in 40 non-DRE urinary exosome-based patient specimens, where narrow stripes indicate a positive biopsy and broad stripes indicate a negative biopsy.

FIGS. 8A-F are bar graphs showing the normalized mRNA readout for 6 markers in 40 urinary exosome based patient specimens, where FIG. 8A shows DLX1, FIG. 8B shows NKX2-3, FIG. 8C shows HOXC4, FIG. 8D shows PCA3, FIG. 8E shows ERG, and FIG. 8F shows PSGR. The specimens were assessed by gene specific RT, TaqMan® based pre-amplification and qRT-PCR assays. The height of the columns indicates normalized expression levels of the relevant genes in the six graphs. Each bar indicates individual patients, wherein narrow stripes indicate a positive biopsy and broad stripes indicate a negative biopsy.

Preliminary analysis showed that the 6-marker assay was evaluable in the urine derived exosome RNA specimens. The mRNA expression was normalized to the prostate marker SPDEF, and an optimal cut-off was determined for each assay.

Figure 9:
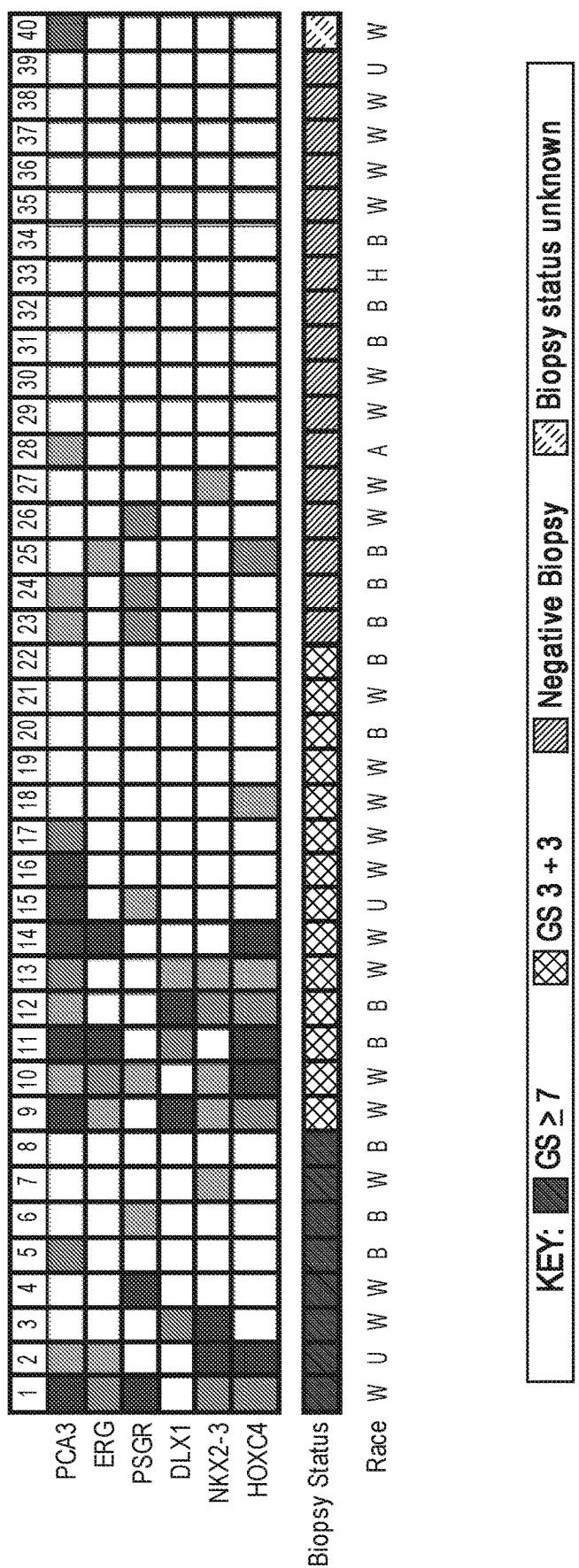
FIG. 9 is a heatmap displaying sensitivity and specificity for 6-marker mRNA expression assay panels (PCA3, ERG, PSGR, DLX1, NKX2-3, and HOXC4) in 40 urinary exosome-based patient specimens. The solid shaded squares represent gene expression levels, wherein higher expression is indicated by darker shades. The biopsy status for each specimen is also shown as either Gleason Score ("GS")>/=7, GS 3+3, negative, or unknown.

FIG. 9 is a heatmap displaying sensitivity and specificity of a 6-marker mRNA expression assay panel in 40 urinary exosome based patient specimens. Column numbers represent individual patients (N=40). Rows represent genes of the panel, race, and biopsy status. The solid shaded squares in FIG. 9 represent gene expression levels, wherein higher expression is indicated by darker shades.

Table 2 below displays the sensitivity and specificity of the 6-marker panel assay illustrated by the heatmap in FIG. 9.

TABLE 2

|  | Biopsy Positive (N = 23) | Biopsy Negative (N = 17) |
| --- | --- | --- |
| Assay Positive | True Positive (N = 18) | False Positive (N = 6) |
| Assay Negative | False Negative (N = 5) | True Negative (N = 11) |

Sensitivity = TP/TP + FN = 18/23 = 78.26%
Specificity = TN/TN + FP = 11/17 = 65.0%

Initial analyses for the combined 6 gene urine marker panel with an optimal cutoff showed a sensitivity of 78.26% and specificity of 65.0% for biopsy results in a feasibility cohort of 40 patients. The urine exosome panel was scored positive in 7 of 8 patients with a biopsy Gleason score of 7 or higher and in 10 of 14 patients with a biopsy Gleason score of 6.

Taken together, these findings demonstrate the identification of a CaP marker panel that is over-expressed equally well in AA and CA CaP tissue, and the development of a non-invasive, urine exosome RNA based gene expression assay platform, which has been successfully evaluated for detecting prostate cancer in AA and CA patients.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed:

1. A method of obtaining a gene expression profile in a biological sample from a patient, the method comprising:
    detecting expression of a plurality of genes in a biological sample obtained from the patient, wherein the plurality of genes consists of PCA3, PCGEM1, and optionally a control gene, and wherein the biological sample comprises exosomes or nucleic acids isolated from exosomes obtained from a non-DRE urine sample.

2. The method of claim 1, wherein nucleic acid expression is detected.

3. The method of claim 1, wherein the method further comprises a step of extracting RNA from exosomes in the non-DRE urine sample prior to the step of detecting expression of the plurality of genes.

4. The method of claim 3, further comprising reverse transcribing the extracted RNA to obtain a cDNA and amplifying the cDNA prior to the step of detecting expression of the plurality of genes.

5. The method of claim 1, wherein the control gene is a housekeeping gene chosen from SPDEF or PSA.

* * * * *